(12) United States Patent
Saito

(10) Patent No.: US 8,986,213 B2
(45) Date of Patent: *Mar. 24, 2015

(54) ULTRASONIC PROBE

(71) Applicant: Konica Minolta, Inc., Tokyo (JP)

(72) Inventor: Koetsu Saito, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/875,764

(22) Filed: May 2, 2013

(65) Prior Publication Data

US 2013/0245453 A1     Sep. 19, 2013

Related U.S. Application Data

(63) Continuation of application No. 12/162,584, filed as application No. PCT/JP2007/051191 on Jan. 25, 2007, now Pat. No. 8,454,518.

(30) Foreign Application Priority Data

Jan. 31, 2006   (JP) .................................. 2006-023169
Jan. 31, 2006   (JP) .................................. 2006-023170

(51) Int. Cl.
*A61B 8/14*       (2006.01)
*A61B 8/00*       (2006.01)
*G10K 11/02*      (2006.01)

(52) U.S. Cl.
CPC ................. *A61B 8/4444* (2013.01); *A61B 8/00* (2013.01); *G10K 11/02* (2013.01)
USPC ....................................... 600/459

(58) Field of Classification Search
USPC ........................................ 600/407, 437, 459
See application file for complete search history.

(56) References Cited

U.S. PATENT DOCUMENTS

| | | | |
|---|---|---|---|
| 4,901,729 A | 2/1990 | Saitoh et al. | |
| 5,115,809 A | 5/1992 | Saitoh et al. | |
| 5,726,952 A | 3/1998 | Eckert et al. | |
| 2001/0021807 A1* | 9/2001 | Saito et al. | .................... 600/437 |
| 2002/0009103 A1 | 1/2002 | Toida | |

(Continued)

FOREIGN PATENT DOCUMENTS

| | | | |
|---|---|---|---|
| JP | 61-240800 A | 10/1986 | |
| JP | 06-253394 A | 9/1994 | |

(Continued)

OTHER PUBLICATIONS

Decision on Grant Patent for Invention Application No. 2008135361/14(045089) dated Jan. 25, 2007.

(Continued)

*Primary Examiner* — Tse Chen
*Assistant Examiner* — Joel F Brutus
(74) *Attorney, Agent, or Firm* — Holtz, Holtz, Goodman & Chick PC

(57) ABSTRACT

An ultrasonic probe includes: a plurality of piezoelectric elements separated from each other by a gap; and an acoustic matching layer formed of a rubber elastic material on a surface of each of the plurality of piezoelectric elements. An acoustic impedance of the rubber elastic material is smaller than an acoustic impedance of the piezoelectric elements and larger than an acoustic impedance of a subject. The acoustic velocity of the rubber elastic material has a value of 1650 msec or less.

33 Claims, 9 Drawing Sheets

(56) References Cited

U.S. PATENT DOCUMENTS

| | | |
|---|---|---|
| 2005/0122004 A1 | 6/2005 | Shibamoto et al. |
| 2005/0165313 A1 | 7/2005 | Byron et al. |
| 2007/0161903 A1 | 7/2007 | Yamashita et al. |

FOREIGN PATENT DOCUMENTS

| | | |
|---|---|---|
| JP | 07-37107 U | 7/1995 |
| JP | 09-084194 A | 3/1997 |
| JP | 10-056694 A | 2/1998 |
| JP | 2000-014672 A | 1/2000 |
| JP | 2000-094665 A | 4/2000 |
| JP | 2003-125494 A | 4/2003 |
| JP | 2004-120283 A | 4/2004 |
| JP | 2005-198261 A | 7/2005 |
| JP | 2005-277988 A | 10/2005 |
| RU | 4674 U1 | 8/1997 |
| RU | 2232547 C2 | 7/2004 |

OTHER PUBLICATIONS

L.V. Osipov; Ultrasonic diagnostic apparatuses; M., Vidar 1999, pp. 40-41.

Takeshi Inoue, et al., "Design of Ultrasonic Transducers with Multiple Acoustic Matching Layers for Medical Application", IEEE Transactions on Ultrasonics, Ferroelectrics, and Frequency Control, Jan. 1987. vol. UFFC-34, No. 1.

International Search Report for PCT/JP2007/051191 dated Apr. 26, 2007.

Indian Office Action dated Jan. 30, 2014 in counterpart Indian Application No. 4017/CHENP/2008.

Korean Office Action dated Apr. 24, 2014 in counterpart Korean Application No. 10-2013-7013583.

\* cited by examiner

FIG. 8
FIG. 9A
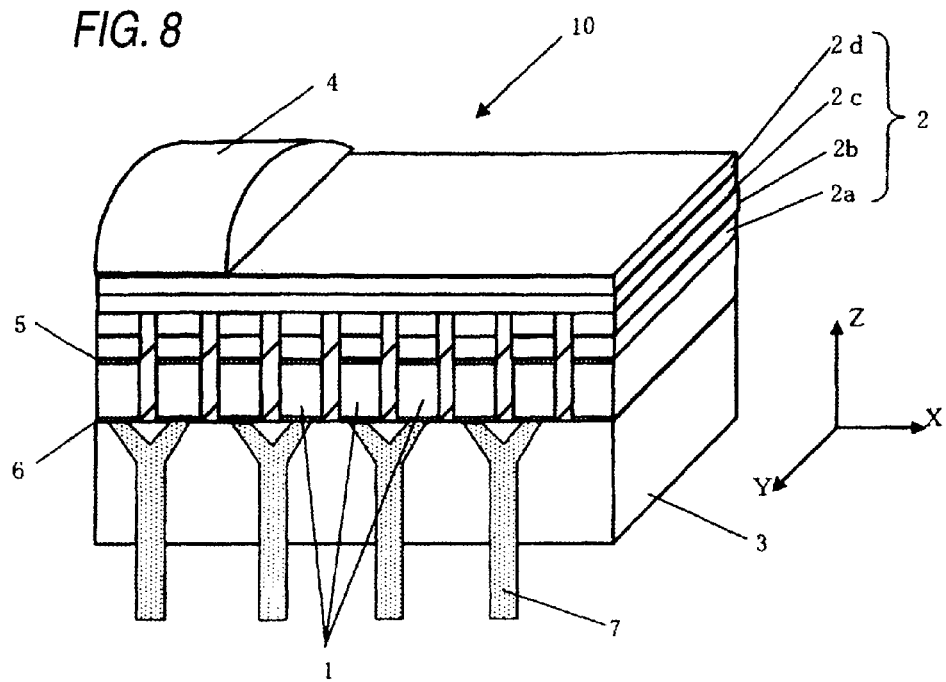
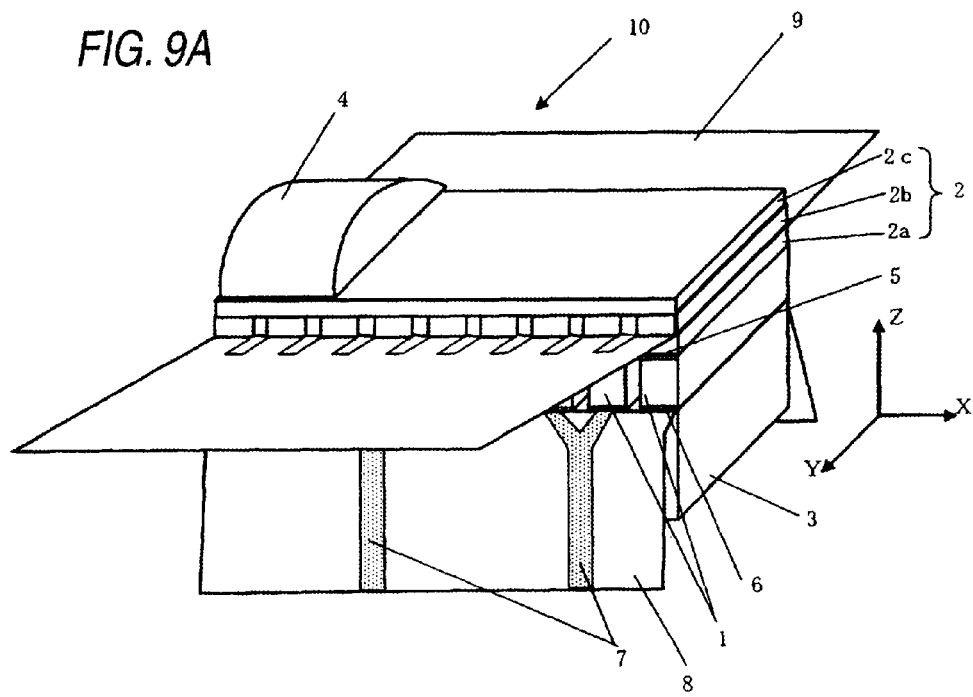

ULTRASONIC PROBE

REFERENCE TO RELATED APPLICATIONS

This application is a continuation of U.S. patent application Ser. No. 12/162,584, filed on Jul. 29, 2008, which is the U.S. National Phase under 35 U.S.C. §371 of International Application No. PCT/JP2007/051191, filed on Jan. 25, 2007, which claims priority from Japanese Patent Application Nos. 2006-023169 and 2006-023170, both filed on Jan. 31, 2006, the entire contents of which are incorporated herein by reference.

TECHNICAL FIELD

The present invention relates to an ultrasonic probe used for transmission and reception of ultrasonic waves to and from a subject such as a living body.

BACKGROUND ART

An ultrasonic diagnostic apparatus irradiates ultrasonic waves to the inside of a subject, especially a living body, such as a person or an animal to detect an echo signal reflected from the inside of the living body and then displays tomographic images of tissues inside the living body, thereby providing information necessary for diagnosis of the subject. In such a case, the ultrasonic diagnostic apparatus uses an ultrasonic probe in order to transmit the ultrasonic waves to the inside of the subject and receive the echo signal from the inside of the subject.

FIG. 12 illustrates an example of such an ultrasonic probe. In FIG. 12, an ultrasonic probe 20 is configured to include a plurality of piezoelectric elements 11 arranged in a predetermined direction so as to transmit and receive ultrasonic waves to and from a subject (not shown), one or more (three layers are illustrated) acoustic matching layer 12 (12a, 12b and 12c) provided on a front surface (upper surface in FIG. 12) at a subject side of the piezoelectric elements 11, an acoustic lens 13 provided on a surface at the subject side of the acoustic matching layer 12, and a backing load member 14 provided on a rear surface of the piezoelectric elements 11 at a side opposite to the acoustic matching layer 12.

Unillustrated electrodes are disposed on the front surface and the rear surface of the piezoelectric elements 11, respectively so that electric signals can be transmitted and received to and from the piezoelectric elements 11. The piezoelectric elements 11 are formed of PZT-based piezoelectric ceramic materials, or single-crystal piezoelectric materials, a piezoelectric composite made of the materials and polymers, or piezoelectric polymers typified by PVDF or the like. The piezoelectric elements 11 are configured to convert a voltage into ultrasonic waves to be transmitted to the inside of the subject or to convert an echo signal reflected from the inside of the subject into an electric signal to be received thereto. In the illustrated example, the plurality of piezoelectric elements 11 is arranged in the X direction. Such an arrangement of the plurality of piezoelectric elements 11 allows electronically scanning ultrasonic waves to be deflected or converged, thereby enabling a so-called electronic scanning.

The acoustic matching layer 12 is provided in order to efficiently transmit and receive ultrasonic waves to and from the inside of the subject. More specifically, the acoustic matching layer 12 performs a function of gradually matching an acoustic impedance of the piezoelectric elements 11 to an acoustic impedance of the subject. In the illustrated example, although three acoustic matching layers 12a, 12b, and 12c are provided, the acoustic matching layers may have one, two, or four or more layers. Moreover, in the illustrated example, although the acoustic matching layer 12 is integrally formed on the plurality of piezoelectric elements 11, the acoustic matching layer 12 is divided so as to correspond to the respective piezoelectric elements 11. Furthermore, there is known a structure that can increase the directivity of ultrasonic waves (for example, see Patent Documents 1 and 2).

The acoustic lens 13 performs a function of condensing an ultrasonic beam in order to increase resolution of a diagnostic image. In the illustrated example, the acoustic lens 13 extends in the Y direction shown in the drawing (a direction orthogonal to the arrangement direction X of the piezoelectric elements 11) with a semi-circular shape that is convex in the Z direction, and is capable of narrowing the ultrasonic waves in the Y direction. The acoustic lens 13 is an optional element and thus will be provided as necessary.

The backing load member 14 performs a function of holding the piezoelectric elements 11 by being coupled to them and attenuating unnecessary ultrasonic waves. In the drawings of this specification, the X direction will be referred to as "the arrangement direction (of the piezoelectric elements)," the Y direction will be referred to as "the width direction (of the piezoelectric elements)," and the Z direction will be referred to as "the thickness direction (of the piezoelectric elements)."

Patent Document 1: Japanese Patent Application Laid-Open Publication No. 2003-125494

Patent Document 2: Japanese Patent Application Laid-Open Publication No. 2005-198261

DISCLOSURE OF THE INVENTION

Problems to be Solved by the Invention

In such an electronic scanning type ultrasonic diagnostic apparatus, piezoelectric elements are grouped arbitrarily and individual piezoelectric elements are driven with a predetermined delay time, so that ultrasonic waves are transmit and received between the piezoelectric elements and a subject. By having such a delay time, the ultrasonic waves are converged or diverged, and it is thus possible to provide an ultrasonic image having a broad viewing width or high resolution.

Such a configuration is already known as a generalized system. In order for an ultrasonic probe to be able to provide such a high-resolution ultrasonic image, it is important to increase the directivity of the ultrasonic beam radiated to the subject through the acoustic matching layer, and moreover, the acoustic lens, as necessary, from the individual ones of the plurality of piezoelectric elements arranged in a predetermined direction, performing electronic scanning.

The electronic scanning type ultrasonic probe is configured to delay respective transmission and reception times of piezoelectric elements (for example, 64 elements) belonging to an arbitrary one of a plurality of groups to perform phase control, so that the ultrasonic beam is focused at a desired position and narrowed for higher resolution imaging, or the ultrasonic beam is deflected to be scanned in a fan-like shape.

In such a case, when the number of piezoelectric elements used in each group is increased (for example, from 64 elements to 96 elements), the aperture of the ultrasonic beam is increased correspondingly, and thus the beam can be condensed strongly, that is, narrowed much more, with the result that it is possible to provide improved resolution.

However, if the directivity of the individual piezoelectric elements is not broad, no matter how much the aperture is increased (the number of elements to which electric signals are applied with delay is increased), non-contributing piezoelectric elements may be present, with the result that the aperture is narrowed and it is thus impossible to narrow and condense the ultrasonic beam. In this regard, in order to increase the aperture, it is desirable to increase the directivity of the piezoelectric elements.

As one measure for increasing the directivity, Patent Document 1 discloses a configuration in which the entire acoustic matching layers are divided so as to correspond to a plurality of piezoelectric elements arranged in a predetermined direction, and in which acoustic coupling between adjacent ones of the piezoelectric elements and between the acoustic matching layers is suppressed as much as possible.

However, in the above-mentioned configuration, it is necessary to divide and arrange the piezoelectric elements for each of the acoustic matching layers, and when the number of acoustic matching layers is increased in order to increase the frequency bandwidth of ultrasonic waves, the division processing is complicated, and it is thus difficult to provide an ultrasonic probe having stable characteristics.

In recent years, the frequency bandwidth used in the ultrasonic probe is becoming broad and a plurality of frequencies is often used. In this respect, in order to obtain a high-resolution ultrasonic image, it is increasingly important to increase the directivity of the ultrasonic probe while providing a broader bandwidth.

The present invention has been made in view of the problems encountered in the conventional examples, and an object of the present invention is to provide an ultrasonic probe which is easy to process and capable of obtaining a high-resolution image.

Means for Solving the Problems

According to the present invention, there is provided an ultrasonic probe including a plurality of piezoelectric elements; and an acoustic matching layer formed of a rubber elastic material, provided on one surface of the plurality of piezoelectric elements.

According to the configuration described above, since the acoustic matching layer is provided in a non-divided state, it is not necessary to process and divide the acoustic matching layer together with the piezoelectric elements, and thus it is possible to eliminate difficulties in processing and to provide a stable ultrasonic probe. Moreover, since the acoustic matching layer is formed of a rubber elastic material, it is possible to provide directivity characteristics equal to or broader than those of the configuration where the acoustic matching layer is divided. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Moreover, the ultrasonic probe according to the present invention is configured such that an acoustic impedance of the rubber elastic material is smaller than an acoustic impedance of the piezoelectric elements and larger than an acoustic impedance of the subject.

According to the configuration described above, since the acoustic impedance of the rubber elastic material is smaller than the acoustic impedance of the piezoelectric elements and larger than the acoustic impedance of the subject, the acoustic impedance of the piezoelectric can be gradually approached to the acoustic impedance of the subject, and thus, ultrasonic waves can be transmitted to and received from the inside of the subject in an efficient manner.

Moreover, the ultrasonic probe according to the present invention is configured such that an acoustic velocity of the acoustic matching layer has a value of 1650 msec or less.

According to the configuration described above, since the acoustic velocity of the acoustic matching layer has a value of 1650 msec or less, even when the acoustic matching layer is not divided, it is possible to provide directivity characteristics equal to or broader than those of a configuration where the acoustic matching layer is divided.

Moreover, the ultrasonic probe according to the present invention is configured to further include an acoustic matching layer disposed between the acoustic matching layer and the plurality of piezoelectric elements and individually arranged so as to correspond to the respective piezoelectric elements.

According to the configuration described above, since only the acoustic matching layer disposed close to the piezoelectric elements is divided in a manner similar to the piezoelectric elements, even when the piezoelectric elements are divided into narrow intervals (for example, 0.1 mm), the processing can be performed in a stable manner, and thus, it is possible to fabricate the ultrasonic probe in a uniform and precise manner. Moreover, since the divided acoustic matching layer is provided between the flat acoustic matching layer and the plurality of piezoelectric elements, the acoustic impedance of the piezoelectric can be gradually approached to the acoustic impedance of the subject, and thus, ultrasonic waves can be transmitted to and received from the inside of the subject in an efficient manner.

According to the present invention, there is provided an ultrasonic probe including a plurality of piezoelectric elements; a third acoustic matching layer provided on one surface of the plurality of piezoelectric elements and having an acoustic impedance in the range of 1.8 to 2.2 MRayls and an acoustic velocity of 1650 msec or less; and first and second acoustic matching layers provided between the third acoustic matching layer and the plurality of piezoelectric elements.

According to the configuration described above, since the third acoustic matching layer has an acoustic impedance in the range of 1.8 to 2.2 MRayls and an acoustic velocity of 1650 msec or less, and the first and second acoustic matching layers are provided, the acoustic impedance of the piezoelectric can be gradually approached to the acoustic impedance of the subject, and thus, ultrasonic waves can be transmitted to and received from the inside of the subject in an efficient manner.

Moreover, the ultrasonic probe according to the present invention is configured such that the third acoustic matching layer is provided on one surface of the plurality of piezoelectric elements, and the first and second acoustic matching layers are individually arranged so as to correspond to the respective piezoelectric elements.

According to the configuration described above, since the first and second acoustic matching layers are provided between the third acoustic matching layer and the plurality of piezoelectric elements and are individually arranged so as to correspond to the respective piezoelectric elements, the acoustic impedance of the piezoelectric can be gradually approached to the acoustic impedance of the subject, and thus, ultrasonic waves can be transmitted to and received from the inside of the subject in an efficient manner.

Moreover, the ultrasonic probe according to the present invention is configured such that the third acoustic matching layer is formed of a rubber elastic material.

According to the present invention, there is provided an ultrasonic probe including a plurality of piezoelectric elements; second and third acoustic matching layers provided on one surface of the plurality of piezoelectric elements and having an acoustic velocity of 1650 msec or less; and a first acoustic matching layer provided between the second and third acoustic matching layers and the plurality of piezoelectric elements.

According to the configuration described above, since the second and third acoustic matching layers have an acoustic velocity of 1650 msec or less, it is possible to provide directivity characteristics equal to or broader than those of the configuration where the acoustic matching layer is divided. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Moreover, the ultrasonic probe according to the present invention is configured such that the second and third acoustic matching layers are provided on one surface of the plurality of piezoelectric elements, and the first acoustic matching layer is individually arranged so as to correspond to the respective piezoelectric elements.

According to the configuration described above, since the second and third acoustic matching layers are provided, it is possible to decrease the number of layers of the acoustic matching layer which is to be divided together with the piezoelectric elements, and thus the difficulties in processing can be eliminated, and a stable ultrasonic probe can be obtained.

Moreover, the ultrasonic probe according to the present invention is configured such that the second and third acoustic matching layers are formed of a rubber elastic material.

According to the present invention, there is provided an ultrasonic probe including a plurality of piezoelectric elements; a fourth acoustic matching layer provided on one surface of the plurality of piezoelectric elements and having an acoustic velocity of 1650 msec or less; and first, second and third acoustic matching layers provided between the fourth acoustic matching layer and the plurality of piezoelectric elements.

According to the configuration described above, since the acoustic velocity of the fourth acoustic matching layer has a value of 1650 msec or less, it is possible to provide directivity characteristics equal to or broader than those of the configuration where the acoustic matching layer is divided. Moreover, since the first, second and third acoustic matching layers are provided between the fourth acoustic matching layer and the plurality of piezoelectric elements, the acoustic impedance of the piezoelectric can be gradually approached to the acoustic impedance of the subject, and thus, ultrasonic waves can be transmitted to and received from the inside of the subject in an efficient manner.

Moreover, the ultrasonic probe according to the present invention is configured such that the fourth acoustic matching layer is provided on one surface of the plurality of piezoelectric elements, and the first, second and third acoustic matching layers are individually arranged so as to correspond to the respective piezoelectric elements.

According to the configuration described above, since the fourth acoustic matching layer is provided, it is possible to decrease the number of layers of the acoustic matching layer which is to be divided together with the piezoelectric elements, and thus the difficulties in processing can be eliminated, and a stable ultrasonic probe can be obtained.

Moreover, the ultrasonic probe according to the present invention is configured such that the third and fourth acoustic matching layers are provided on one surface of the plurality of piezoelectric elements, and the first and second acoustic matching layers are individually arranged so as to correspond to the respective piezoelectric elements.

According to the configuration described above, since the third and fourth acoustic matching layers are provided, it is possible to decrease the number of layers of the acoustic matching layer which is to be divided together with the piezoelectric elements, and thus the difficulties in processing can be eliminated, and a stable ultrasonic probe can be obtained.

Moreover, the ultrasonic probe according to the present invention is configured such that the third acoustic matching layer is formed of a rubber elastic material and has an acoustic velocity of 1650 m/sec or less. Furthermore, the ultrasonic probe according to the present invention is configured such that the fourth acoustic matching layer is formed of a rubber elastic material.

According to the configuration described above, since the acoustic matching layer is formed of a rubber elastic material and has an acoustic velocity of 1650 msec or less, it is possible to provide directivity characteristics equal to or broader than those of a configuration where the acoustic matching layer is divided.

According to the present invention, there is provided an ultrasonic probe having a backing load member and a plurality of piezoelectric elements arranged on an upper surface of the backing load member, the ultrasonic probe including: a first polymer film provided between the backing load member and the plurality of piezoelectric elements and provided with electric terminals individually arranged so as to correspond to the respective piezoelectric elements; a first acoustic matching layer provided on an upper surface of the plurality of piezoelectric elements and individually arranged so as to correspond to the respective piezoelectric elements; a second polymer film provided on an upper surface of the first acoustic matching layer and provided with electric terminals individually arranged so as to correspond to the respective piezoelectric elements; a second acoustic matching layer provided on an upper surface of the second polymer film and individually arranged so as to correspond to the respective piezoelectric elements; and a third acoustic matching layer provided on an upper surface of the second acoustic matching layer and formed of a rubber elastic material.

According to the configuration described above, since the third acoustic matching layer is formed of a rubber elastic material, it is possible to provide broader frequency bandwidth and increase the directivity. Moreover, since the third acoustic matching layer is provided in a non-divided state, the number of layers of the acoustic matching layer, which is to be divided together with the piezoelectric elements can be decreased, and thus, it is possible to eliminate difficulties in processing. Furthermore, since the electric terminals are provided to the polymer film, the electric terminals can be formed in an easy manner. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Moreover, the ultrasonic probe according to the present invention is configured such that an acoustic velocity of the third acoustic matching layer has a value of 1650 msec or less. Furthermore, the ultrasonic probe according to the present invention is configured such that an acoustic impedance of the second polymer film is smaller than an acoustic impedance of the second acoustic matching layer and has a thickness of 0.07 wavelength or less at using frequency.

According to the present invention, there is provided an ultrasonic probe having a backing load member and a plurality of piezoelectric elements arranged on an upper surface of the backing load member, the ultrasonic probe including: a first polymer film provided between the backing load member and the plurality of piezoelectric elements and provided with electric terminals; a first acoustic matching layer provided on an upper surface of the plurality of piezoelectric elements and individually arranged so as to correspond to the respective piezoelectric elements; a second polymer film provided on an upper surface of the first acoustic matching layer and provided with electric terminals individually arranged so as to correspond to the respective piezoelectric elements; a second acoustic matching layer provided on an upper surface of the second polymer film and formed of a rubber elastic material; and a third acoustic matching layer provided on an upper surface of the second acoustic matching layer and formed of a rubber elastic material.

According to the configuration described above, since the second and third acoustic matching layers are formed of a rubber elastic material, it is possible to provide broader frequency bandwidth and increase the directivity. Moreover, since the second and third acoustic matching layers are provided in a non-divided state, the number of layers of the acoustic matching layer, which is to be divided together with the piezoelectric elements can be decreased, and thus it is possible to eliminate difficulties in processing. Furthermore, since the electric terminals are provided to the polymer film, the electric terminals can be formed in an easy manner. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Moreover, the ultrasonic probe according to the present invention is configured such that the rubber elastic material is mainly composed of synthetic rubber, silicon rubber, urethane rubber, or elastomer. Furthermore, the ultrasonic probe according to the present invention is configured such that the synthetic rubber is mainly composed of ethylene-propylene copolymer rubber, chloroprene rubber, butadiene rubber, isoprene rubber, styrene-butadiene copolymer rubber, or acrylonitrile-butadiene copolymer rubber.

Advantages of the Invention

According to the present invention, since the acoustic matching layer provided on one surface of the piezoelectric elements is formed of a rubber elastic material, it is not necessary to divide the acoustic matching layer and directivity characteristics equal to or broader than those of the configuration where the acoustic matching layer is divided can be provided. Therefore, it is possible to provide an ultrasonic probe which is easy to process and capable of obtaining a high-resolution diagnostic image.

BRIEF DESCRIPTION OF THE DRAWINGS

FIG. 8 is a schematic perspective view of an ultrasonic probe according to a sixth embodiment of the present invention.

FIG. 9A is a schematic perspective view of the ultrasonic probe according to the first embodiment of the present invention.

DESCRIPTION OF REFERENCE NUMBERS

1: PIEZOELECTRIC ELEMENT
2, 2a, 2b, 2c, 2d: ACOUSTIC MATCHING LAYER
3: BACKING LOAD MEMBER
4: ACOUSTIC LENS
5: GROUND ELECTRODE
6: SIGNAL ELECTRODE
7: ELECTRIC TERMINAL
8, 9: FILM
10: ULTRASONIC PROBE
11: PIEZOELECTRIC ELEMENT
12: ACOUSTIC MATCHING LAYER
13: ACOUSTIC LENS
14: BACKING LOAD MEMBER
20: ULTRASONIC PROBE

BEST MODE FOR CARRYING OUT THE INVENTION

Embodiment 1

Figure 1:
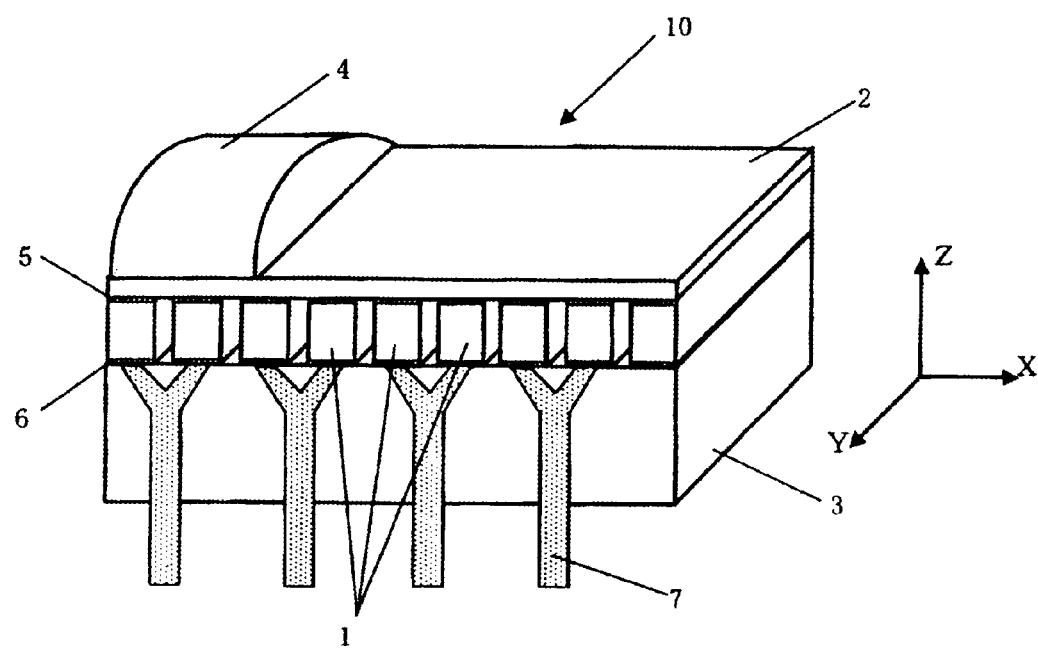
FIG. 1 is a schematic perspective view of an ultrasonic probe according to a first embodiment of the present invention.

Hereinafter, an ultrasonic probe according to a first embodiment of the present invention will be described with reference to the drawings. FIG. 1 is a partially schematic perspective view of an ultrasonic probe 10 according to the first embodiment.

The ultrasonic probe 10 is configured to include a plurality of piezoelectric elements 1, an acoustic matching layer 2 (first acoustic matching layer) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2, and an acoustic lens 4 provided, as necessary, on the acoustic matching layer 2. The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

The electrodes 5 and 6 are electrically connected to an unillustrated ultrasonic diagnostic apparatus through a cable via an electric terminal 7, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the illustrated example, the piezoelectric elements 1 are divided into individual ones, and materials, such as silicon rubber or urethane rubber, capable of reducing acoustic coupling are filled in portions corresponding to the division grooves.

Figure 2:
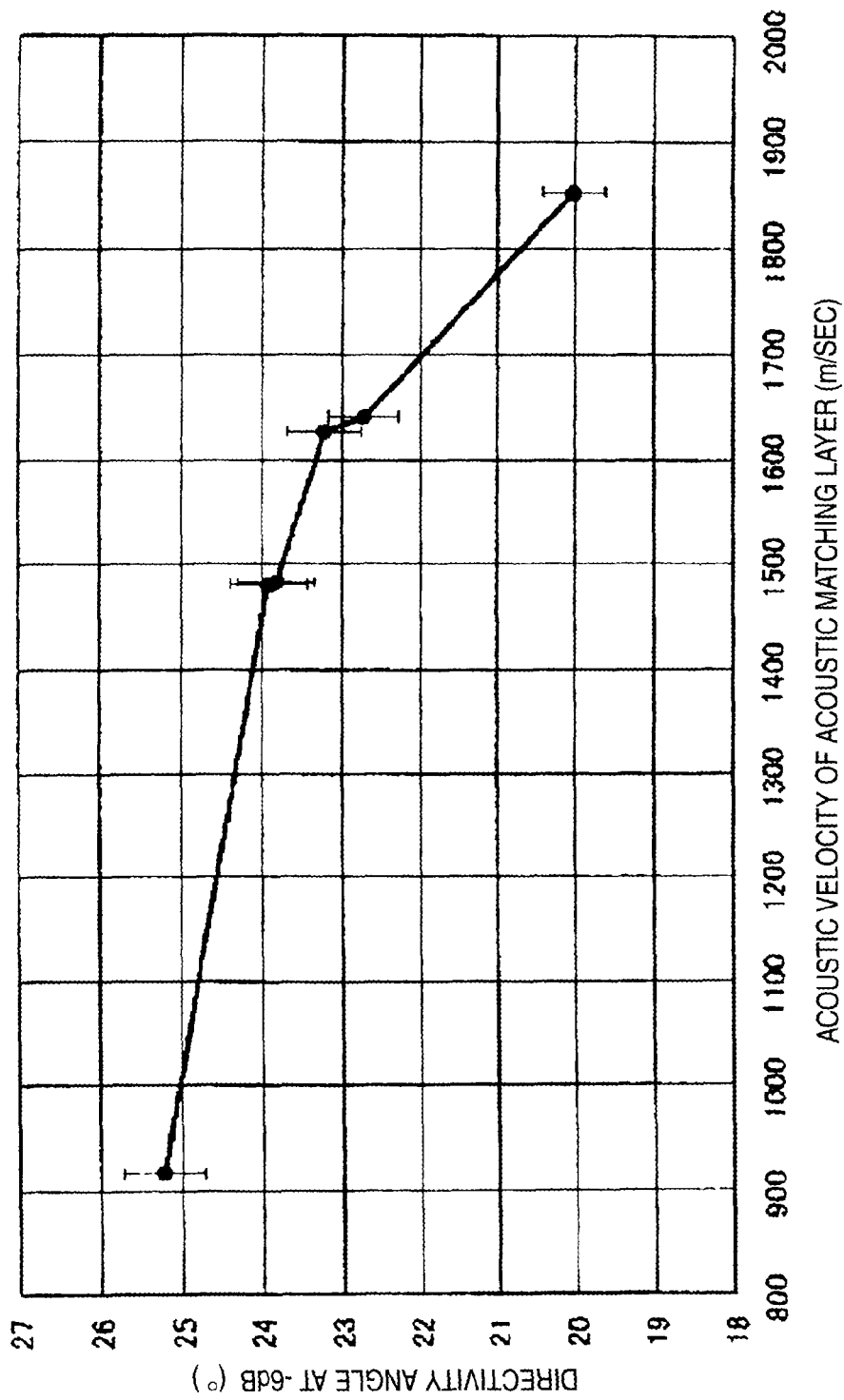
FIG. 2 is a diagram illustrating the relationship between an acoustic velocity and a directivity angle of an acoustic matching layer.

FIG. 2 is a diagram illustrating the relationship between a directivity angle of ultrasonic waves in the arrangement direction X of the plurality of piezoelectric elements 1 illustrated in FIG. 1 and an acoustic velocity of a rubber elastic material of the acoustic matching layer 2. In the ultrasonic probe 10 of a so-called electronic scanning type, having the plurality of piezoelectric elements 1 arranged therein, an important point in increasing the resolution of an ultrasonic image is how the directivity in the X direction of the piezoelectric elements 1 can be increased.

In the first embodiment, as illustrated in FIG. 1, the piezoelectric elements 1 provided on the backing load member 3 are divided by means of a slicing machine or the like, silicon rubber or urethane rubber is filled in the division grooves, and thereafter, the acoustic matching layer 2 of rubber elastic material is provided on the surface of the divided piezoelectric elements 1.

As is known, the acoustic matching layer 2 is formed using a material having an acoustic impedance having an intermediate value between those of the piezoelectric elements 1 and a subject (not shown), and having a thickness basically corresponding to a ¼ wavelength of a using frequency. Further, on the surface of the acoustic matching layer 2, the acoustic lens 4 formed of materials such as silicon rubber is provided, as necessary.

In the prior art, in order to increase the directivity, the acoustic matching layer 2 is placed on the piezoelectric elements 1 and then divided in a manner similar to the piezoelectric elements 1. This is to prevent a situation where ultrasonic waves propagate in the horizontal direction within the acoustic matching layer 2 and thus the directivity is narrowed, because unless the acoustic matching layer 2 is not divided unlike the piezoelectric elements 1, the acoustic matching layer 2 will be continuously connected with each other.

However, when the piezoelectric elements 1, the acoustic matching layer 2, and moreover, a portion of the backing load member 3 are processed together to be divided by a slicing machine, and in particular, with a division gap as narrow as 0.1 mm, there is a problem that since a plurality of materials is processed together, it is difficult to perform the division processing in a uniform and stable manner.

The present embodiment is characterized in that only the piezoelectric elements 1 are divided, and the acoustic matching layer 2 of rubber elastic materials is provided on the surface of the divided piezoelectric elements 1 in a one-layer state where the acoustic matching layer is not divided but connected, so that it is easy to process and the processing can be performed in a uniform and stable manner, and that the resulting directivity is equal to or greater than that obtainable from the configuration where the acoustic matching layer 2 is divided.

The rubber elastic material as the material of the acoustic matching layer 2 uses a material having an acoustic impedance having an intermediate value between those of the piezoelectric elements 1 and the subject and having a thickness basically corresponding to a ¼ wavelength of the using frequency. As a result of the investigation with experiments on various materials, when rubber elastic materials having the same values in hardness and acoustic impedance were used as the acoustic matching layer 2, they showed different directivities.

For example, an angle of the directivity when the piezoelectric elements 1 having a frequency of 3.5 MHz are divided into intervals of 0.38 mm corresponding to the gaps of the divided piezoelectric elements 1 (a state where two parts divided into intervals of 0.19 mm are electrically coupled), as defined at a level of −6 dB, corresponds to a directivity angle of about 23 degrees for a configuration type where the acoustic matching layer 2 is divided together with the piezoelectric elements 1.

That is, a direction in which the strength of an ultrasonic beam radiated in the Z direction decreases by −6 dB corresponds to an angle of about 23 degrees from the Z direction. Moreover, it was configured such that silicon rubber materials are filled in the division grooves of the piezoelectric elements 1 and the acoustic matching layer 2.

In a configuration type where the piezoelectric elements 1 are divided with the same specifications by the above-mentioned method and the acoustic matching layer 2 is not divided as illustrated in FIG. 1, the directivity characteristics of ultrasonic waves in the arrangement direction of the piezoelectric elements 1 were measured in a state where a plurality of acoustic matching layers 2 are prepared, respectively formed of silicon rubber (hardness: 76 on shore A hardness, acoustic velocity: 915 msec, acoustic impedance: 2.1 MRayls), chloroprene rubber (hardness: 70 on shore A hardness, acoustic velocity: 1630 msec, acoustic impedance: 2.16 MRayls), ethylene-propylene copolymer rubber (hardness: 65 on shore A hardness, acoustic velocity: 1480 msec, acoustic impedance: 1.94 MRayls), acrylonitrile-butadiene copolymer rubber (hardness: 60 on shore A hardness, acoustic velocity: 1640 msec, acoustic impedance: 1.97 MRayls), and urethane rubber (hardness: 78 on shore A hardness, acoustic velocity: 1850 msec, acoustic impedance: 1.98 MRayls), and the respective acoustic matching layers 2 are placed on the surface of the piezoelectric elements 1, and an acoustic lens formed of silicon rubber is provided on the upper surface of the acoustic matching layer 2.

As a result of the measurement, it can be concluded that the directivity characteristics changed depending on the materials of the acoustic matching layer 2. Moreover, in the division grooves of the divided piezoelectric elements 1, silicon rubber materials were filled in a manner similar to the configuration where the division is performed up to the acoustic matching layer 2.

Moreover, as a material other than the urethane rubber as mentioned above, a material in which an arbitrary amount of fillers such as alumina, carbon or calcium carbonate is filled in order to adjust an acoustic impedance was used.

The difference in the directivity characteristics of the acoustic matching layers 2 formed of the above-mentioned five kinds of materials was neither correlated with nor influenced by the hardness, the acoustic impedance, and the like of the materials. However, the acoustic velocity characteristics of the materials of the acoustic matching layers 2 had influence on, that is, was correlated with, the directivity characteristics, and showed good correlation.

The relationship between the directivity angle measured at a level of −6 dB using a frequency of 3.5 MHz and an acoustic velocity of the material is illustrated in FIG. 2. As illustrated in FIG. 2, it showed good correlation with an acoustic velocity, and a correlation coefficient was 0.86. In this respect, in the configuration where the acoustic matching layer 2 is not divided, it can be concluded that it is necessary to focus on the acoustic velocity in order to increase the directivity. The directivity angles when the respective materials were used for the acoustic matching layer 2 are as follows.

The respective directivity angles were 25 degrees for the silicon rubber, 23.5 degrees for the chloroprene rubber, 23.5 degrees for the ethylene-propylene copolymer rubber, 22.9 degrees for the acrylonitrile-butadiene copolymer rubber, and 20 degrees for the urethane rubber. Moreover, it is considered that the measurement result has a deviation of about ±0.5 degrees.

When the directivity angles were compared with the directivity angle of the prior art configuration where the acoustic matching layer 2 is divided together with the piezoelectric elements 1, in order to obtain a directivity angle approximately equal to the directivity angle of the prior art configuration, it is necessary to form the acoustic matching layer 2 using a material having an acoustic velocity in the vicinity of 1650 msec. Moreover, in order to increase the directivity, it can be concluded from the result illustrated in FIG. 2 that it is necessary to use a material having an acoustic velocity of 1650 msec or less, for example, a material such as silicon rubber.

Moreover, in the case of the urethane rubber which showed a narrow directivity angle, since among urethane rubbers, some kinds of products (for example, medium-size urethane resin of a grade UE-644, manufactured by SANYU REC Co., Ltd. has an acoustic velocity of 1580 msec and an acoustic impedance of 2.1 MRayls) have an acoustic velocity in the vicinity of 1650 msec or less, it cannot be said that the urethane rubber narrows the directivity angle, and the directivity angle is determined by an acoustic velocity. Therefore, when materials having an acoustic velocity of 1650 msec or less are selected, the materials are basically narrowed down to the rubber elastic materials.

As described above, in the configuration where the acoustic matching layer 2 is not divided unlike the piezoelectric elements 1 but is provided as one sheet of continuous film, in order to secure or increase the directivity, it can be concluded that it is necessary to focus on an acoustic velocity of the material of the acoustic matching layer 2.

For example, a material having an acoustic impedance of about 2 MRayls as the materials mentioned above is not limited to the rubber elastic materials but plastic materials are also usable. For example, materials in which filling materials are filled in polyethylene resin, polystyrene resin, or the epoxy resin described in Patent Document 2 may be used, and such materials have an acoustic velocity of about 1800 msec or more. When the acoustic matching layer 2 is formed of such materials and is not divided similar to the configuration of the present embodiment, the directivity is narrowed, as is clearly understood from the relationship shown in FIG. 2. Therefore, when such materials are used, it is necessary to configure such that the acoustic matching layer 2 is divided in a manner similar to the piezoelectric elements 1, so that the directivity is increased.

Moreover, although it has been described for the case where the acoustic matching layer 2 is mainly composed of synthetic rubbers such as chloroprene rubber, ethylene-propylene copolymer rubber, and acrylonitrile-butadiene copolymer rubber, the same advantages can be obtained when the acoustic matching layer 2 is mainly composed of other synthetic rubber materials such as butadiene rubber, isoprene rubber, styrene-butadiene copolymer rubber or acryl rubber.

Furthermore, although it has been described for the case where the acoustic matching layer 2 is mainly composed of a rubber elastic material such as synthetic rubber, silicon rubber or urethane rubber, the same advantages can be obtained when the acoustic matching layer 2 is formed of other elastomeric materials having a rubber elastic material.

In addition, although the first embodiment has been described for the case where the piezoelectric elements are arranged in a one-dimensional manner, the same advantages can be obtained when the piezoelectric elements are arranged in a two-dimensional manner. Moreover, although the first embodiment has been described for the case where a plurality of piezoelectric elements is arranged, a rubber elastic material may be used for the acoustic matching layer even when the piezoelectric elements are not arranged but form a single body.

Furthermore, although the first embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Embodiment 2

Figure 3:
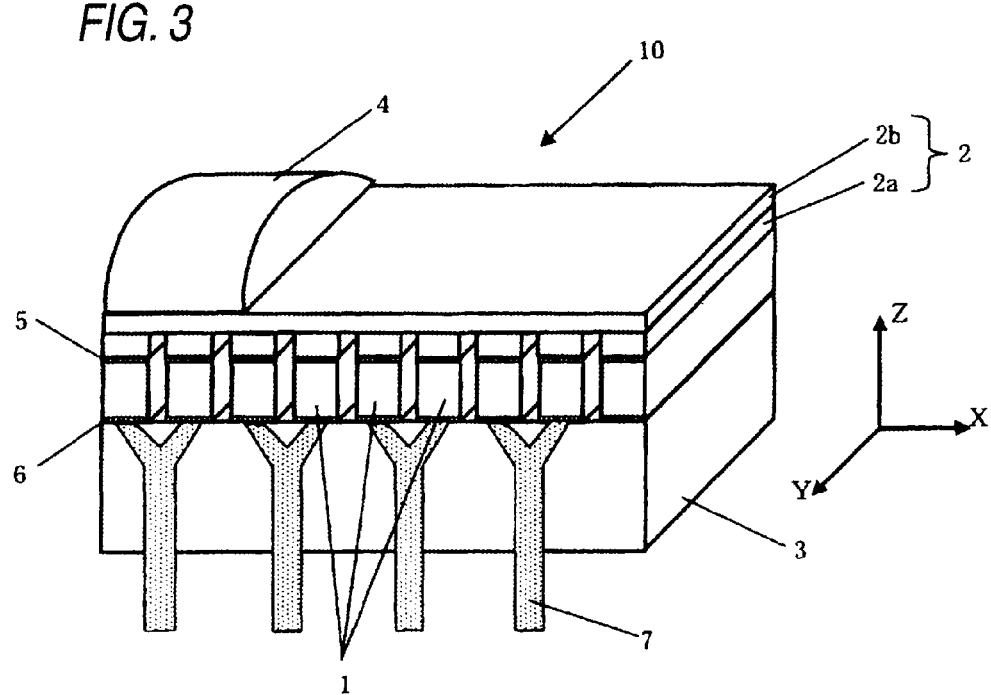
FIG. 3 is a schematic perspective view of an ultrasonic probe according to a second embodiment of the present invention.

Hereinafter, an ultrasonic probe according to a second embodiment of the present invention will be described with reference to the drawings. FIG. 3 is a partially schematic perspective view of an ultrasonic probe 10 according to the second embodiment.

The ultrasonic probe 10 is configured to include a plurality of piezoelectric elements 1, a two-layered acoustic matching layer 2 (2*a* and 2*b*) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2*a* and 2*b*), and an acoustic lens 4 provided, as necessary, on the acoustic matching layer 2 (2*a* and 2*b*). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

The electrodes 5 and 6 are electrically connected to an unillustrated ultrasonic diagnostic apparatus through a cable via an electric terminal 7, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the illustrated example, the piezoelectric elements 1 and a first acoustic matching layer 2*a* disposed close to the piezoelectric elements 1 are divided into individual ones, and materials, such as silicon rubber or urethane rubber, capable of reducing acoustic coupling are filled in portions corresponding to the division grooves. Moreover, a second acoustic matching layer 2b is provided as one sheet of non-divided, continuous film on an upper surface of the acoustic matching layer 2a disposed close to the piezoelectric elements 1. In addition, an acoustic lens is provided as necessary by using materials such as silicon rubber.

In the ultrasonic probe 10 of a so-called electronic scanning type, having the plurality of piezoelectric elements 1 arranged therein, similar to the first embodiment, an important point in increasing the resolution of an ultrasonic image is how the directivity in the X direction of the piezoelectric elements 1 can be increased.

Although the first embodiment has been described for the case where the acoustic matching layer 2 has a single layer, when a difference between respective acoustic impedance of the piezoelectric elements 1 and a subject is large, for example, when PZT-based piezoelectric ceramic materials having an acoustic impedance of about 30 MRayls are used for the piezoelectric elements, the difference is large because the subject has an acoustic impedance of about 1.5 MRayls; therefore, there is a limit in increasing the frequency bandwidth in such a single-layer acoustic matching layer. Therefore, it is necessary to configure the acoustic matching layer 2 to have two or more layers in order to increase the bandwidth.

However, when the acoustic matching layer is configured to have two or more layers, it was difficult to increase the directivity unless the acoustic matching layer 2 is divided in a manner similar to the piezoelectric elements 1. This is because the acoustic matching layer 2 is divided by a slicing machine or the like in a manner similar to the piezoelectric elements 1, the thickness increases as the number of layers of the acoustic matching layer 2 increases, and because the number of materials of the layers to be divided increases, the division process is complicated, and thus, it is difficult to perform the division processing in a uniform and stable manner. The present embodiment relates to a configuration that solves such a problem to thereby increase the directivity.

In the present embodiment, the acoustic matching layer is configured to have two or more layers (in the illustrated example, two layers), and as illustrated in FIG. 3, the piezoelectric elements 1 and the acoustic matching layer 2a disposed close to the piezoelectric elements 1 are divided, and a continuous single-layered acoustic matching layer 2b is provided on an upper surface of the acoustic matching layer 2a.

As materials of the piezoelectric elements 1, PZT-based piezoelectric ceramic materials, PZN-PT-based or PMN-PT-based single-crystal piezoelectric materials, or a piezoelectric composite made of the materials and polymers are used. As materials of the acoustic matching layer 2a, graphite or epoxy resin in which fillers such as metal or oxides are filled is used.

Moreover, as materials of the acoustic matching layer 2b, materials mainly composed of the same rubber elastic material as described in the first embodiment, such as silicon rubber, chloroprene rubber, ethylene-propylene copolymer rubber, acrylonitrile-butadiene copolymer rubber, and urethane rubber are used.

When it is desired to make the acoustic matching layer 2b have an acoustic impedance having a value different from that of the first embodiment, the acoustic impedance can be adjusted by filling fillers such as metal or oxides in a main component material of the rubber elastic material.

Here, the premise in providing the acoustic matching layer 2b as one sheet of non-divided and continuous film is to select a rubber elastic material capable of providing directivity characteristics equal to or better than those of the configuration where the acoustic matching layer 2b is divided and having an acoustic velocity of 1650 msec or less. This can be clearly understood from the result illustrated in FIG. 2 and described in the first embodiment.

In this way, it is possible to decrease the number of layers of the acoustic matching layer which is to be divided in a manner similar to the piezoelectric elements 1. Therefore, even when they are divided into narrow intervals (for example, 0.1 mm), the processing can be performed in a stable manner, and thus, it is possible to fabricate the ultrasonic probe in a uniform and precise manner without decreasing the directivity.

As described above, in the configuration where the acoustic matching layer 2a of the two-layered acoustic matching layer 2 disposed close to the piezoelectric elements 1 is divided in a manner similar to the piezoelectric elements 1, and the continuous, single-layered acoustic matching layer 2b is provided on the upper surface of the acoustic matching layer 2a, it is necessary to focus on the acoustic velocity of the material of the acoustic matching layer 2b in order to secure or increase the directivity.

For example, the materials of the acoustic matching layer 2b are not limited to the rubber elastic materials but plastic materials are also usable. For example, materials in which filling materials are filled in polyethylene resin, polystyrene resin, polyimide resin, epoxy resin, or a material in which filling materials are filled in the epoxy resin described in Patent Document 2 may be used, and such materials have an acoustic velocity of about 1800 msec or more. When the acoustic matching layer 2 is formed of such materials and is not divided similar to the configuration of the present embodiment, the directivity angle is narrowed, as is clearly understood from the result shown in FIG. 2. Therefore, when such materials are used, it is necessary to divide the acoustic matching layer 2b in a manner similar to the piezoelectric elements 1 and the acoustic matching layer 2a.

Moreover, although the second embodiment has been described for the case where the acoustic matching layer 2b is formed of synthetic rubbers such as chloroprene rubber, ethylene-propylene copolymer rubber, and acrylonitrile-butadiene copolymer rubber, the same advantages can be obtained when the acoustic matching layer 2b is mainly composed of other synthetic rubber materials such as butadiene rubber, isoprene rubber, styrene-butadiene copolymer rubber or acryl rubber.

Furthermore, although the second embodiment has been described for the case where the acoustic matching layer 2b is formed of a rubber elastic material such as synthetic rubber, silicon rubber or urethane rubber, the same advantages can be obtained when the acoustic matching layer 2b is formed of other elastomeric materials having a rubber elastic material.

Furthermore, although the second embodiment has been described for the case where the acoustic matching layer 2 has two layers, the same advantages can be obtained when the acoustic matching layer has three or more layers, and an acoustic matching layer disposed close to the subject is not divided but formed as a continuous body by using a rubber elastic material.

In addition, although the second embodiment has been described for the case where the piezoelectric elements are arranged in a one-dimensional manner, the same advantages can be obtained when the piezoelectric elements are arranged in a two-dimensional manner. Moreover, although the second embodiment has been described for the case where a plurality of piezoelectric elements is arranged, a rubber elastic material may be used for the acoustic matching layer even when the piezoelectric elements are not arranged but form a single body.

Furthermore, although the second embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Embodiment 3

Figure 4:
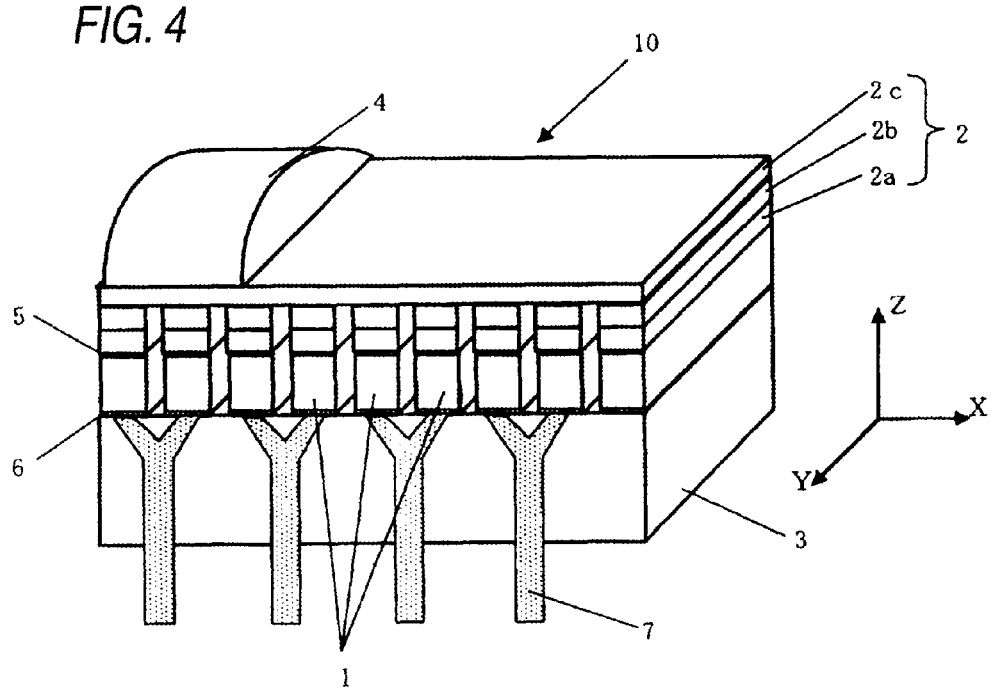
FIG. 4 is a schematic perspective view of an ultrasonic probe according to a third embodiment of the present invention.

Hereinafter, an ultrasonic probe according to a third embodiment of the present invention will be described with reference to the drawings. FIG. 4 is a partially schematic perspective view of an ultrasonic probe 10 according to the third embodiment.

The ultrasonic probe 10 is configured to include a plurality of piezoelectric elements 1, a three-layered acoustic matching layer 2 (2a, 2b and 2c) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2a, 2b and 2c), and an acoustic lens 4 provided, as necessary, on the acoustic matching layer 2 (2a, 2b and 2c). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

The electrodes 5 and 6 are electrically connected to an unillustrated ultrasonic diagnostic apparatus through a cable via an electric terminal 7, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the illustrated example, the piezoelectric elements 1, a first acoustic matching layer 2a, and a second acoustic matching layer 2b, each layer being disposed close to the piezoelectric elements 1 are divided into individual ones, and materials, such as silicon rubber or urethane rubber, capable of reducing acoustic coupling are filled in portions corresponding to the division grooves. Moreover, a third acoustic matching layer 2c is provided as one sheet of non-divided, continuous film on an upper surface of the second acoustic matching layer 2b. In addition, an acoustic lens is provided as necessary by using materials such as silicon rubber.

In the ultrasonic probe 10 of a so-called electronic scanning type, having the plurality of piezoelectric elements 1 arranged therein, similar to the second embodiment, an important point in increasing the resolution of an ultrasonic image is how the directivity in the X direction of the piezoelectric elements 1 can be increased.

While the second embodiment has been described for the case where the acoustic matching layer 2 has two layers, since the acoustic matching layer 2 is configured to have three layers, it is possible to further increase the bandwidth. However, when the acoustic matching layer is configured to have three or more layers, as described in Patent Documents 1 and 2, it was difficult to increase the directivity unless the acoustic matching layer 2 (2a, 2b and 2c) is divided in a manner similar to the piezoelectric elements 1.

This is because the acoustic matching layer 2 is divided by a slicing machine or the like in a manner similar to the piezoelectric elements 1, the thickness increases as the number of layers of the acoustic matching layer 2 increases, and because the number of materials of the layers to be divided increases, the division process is complicated, and thus, it is difficult to perform the division processing in a uniform and stable manner. The present embodiment relates to a configuration that solves such a problem to thereby provide a broader bandwidth and increase the directivity.

In the present embodiment, the acoustic matching layer is configured to have three layers, and as illustrated in FIG. 4, the piezoelectric elements 1 and the first and second acoustic matching layers 2a and 2b disposed close to the piezoelectric elements 1 are divided, and a third continuous single-layered acoustic matching layer 2c is provided on an upper surface of the first acoustic matching layer 2a and the second acoustic matching layer 2b.

As materials of the piezoelectric elements 1, PZT-based piezoelectric ceramic materials, PZN-PT-based or PMN-PT-based single-crystal piezoelectric materials, or a piezoelectric composite made of the materials and polymers are used. As materials of the first acoustic matching layer 2a, materials such as glass, such as single-crystal silicon, crystal or molten quartz, machinable ceramics, or graphite, having an acoustic impedance value ranging from 8 to 20 MRayls are used. As materials of the second acoustic matching layer 2b, materials such as graphite or epoxy resin in which fillers such as metal or oxides are filled, having an acoustic impedance value ranging from 3 to 8 MRayls are used.

Moreover, as materials of the third acoustic matching layer 2c, materials mainly composed of a rubber elastic material, such as silicon rubber, chloroprene rubber, ethylene-propylene copolymer rubber, acrylonitrile-butadiene copolymer rubber, and urethane rubber are used.

The respective acoustic impedances of the acoustic matching layer 2 (2a, 2b and 2c) are determined by the respective materials or frequency characteristics thereof. For example, the frequency characteristics were calculated in a configuration where the frequency was set to a central frequency of 3.5 MHz, a material having an acoustic impedance of 7 MRayls was used for the backing load member 3, a PZT-based piezoelectric ceramic material such as PZT-5H was used for the piezoelectric elements 1, graphite having an acoustic impedance of 9 MRayls was used for the first acoustic matching layer 2a, and epoxy resin in which oxides having an acoustic impedance of 4 MRayls are filled was used for the second acoustic matching layer 2b, so that the acoustic impedance of the third acoustic matching layer 2c is varied in the range of 1.5 to 2.5 MRayls.

Figure 5:
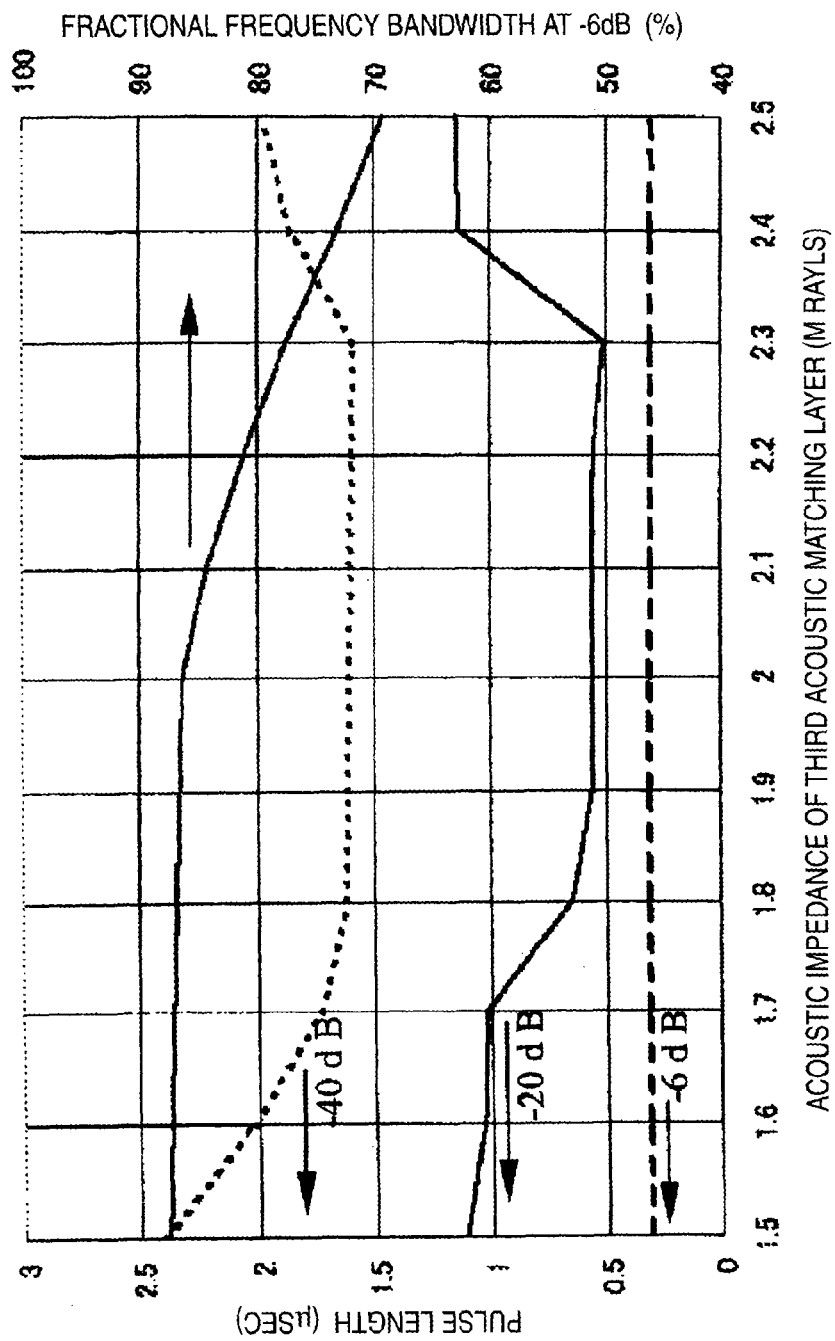
FIG. 5 is a diagram illustrating the relationship between an acoustic impedance, a pulse length, and a fractional bandwidth of a third acoustic matching layer.

The relationship between a fractional bandwidth of the frequency characteristics at −6 dB and a pulse length, evaluated at levels of −6 dB, −20 dB, and −40 dB is illustrated in FIG. 5. In FIG. 5, a horizontal axis represents an acoustic impedance of the third acoustic matching layer 2c, the left vertical axis represents a pulse length, and the right vertical axis represents a fractional frequency bandwidth (bandwidth/central frequency) at −6 dB.

As will be clearly understood from FIG. 5, the pulse length is scarcely changed at a level of −6 dB when the acoustic impedance of the third acoustic matching layer 2c varies; however, the pulse length is changed at levels of −20 dB and −40 dB and has a small value when the acoustic impedance is in the range of 1.8 to 2.3 MRayls. Since the resolution increases advantageously as the pulse length has smaller values, decreasing the pulse width is important in increasing the resolution.

On the other hand, as the fractional bandwidth increases, a resolution and a diagnostic depth increase. Looking into the fractional frequency bandwidth illustrated in FIG. 5, it can be known that when the acoustic impedance of the third acoustic matching layer 2c increases greater than about 2.3 MRayls, the fractional bandwidth becomes 80 percents or less, and it is thus difficult to provide a broader bandwidth. Therefore, from the result of the characteristics of the pulse length and the fractional bandwidth, it can be concluded that the acoustic impedance of the third acoustic matching layer 2c is preferably in the range of 1.8 to 2.2 MRayls.

As materials of the third acoustic matching layer 2c having an acoustic impedance in the range of 1.8 to 2.2 MRayls, a material which can provide the acoustic impedance of that range solely as a main component material of a rubber elastic material can be used, per se; however, a material having an acoustic impedance value outside that range may be filled with fillers or the like in order to adjust the acoustic impedance.

Here, the premise in providing the third acoustic matching layer 2c as one sheet of non-divided and continuous film is to select a rubber elastic material capable of providing directivity characteristics equal to or better than those of the configuration where the third acoustic matching layer 2c is divided and having an acoustic velocity of 1650 msec or less. This can be clearly understood from the result illustrated in FIG. 2 and described in the first embodiment.

In this way, it is possible to decrease the number of layers of the acoustic matching layer which is to be divided in a manner similar to the piezoelectric elements 1. Therefore, even when they are divided into narrow intervals (for example, 0.1 mm), the processing can be performed in a stable manner, and thus, it is possible to fabricate the ultrasonic probe in a uniform and precise manner without decreasing the directivity.

As described above, in the configuration where the first and second acoustic matching layers 2a and 2b of the three-layered acoustic matching layer 2 disposed close to the piezoelectric elements 1 are divided in a manner similar to the piezoelectric elements 1, and the third continuous, single-layered acoustic matching layer 2c is provided on the upper surface of the second acoustic matching layer 2b, it is necessary to focus on the acoustic velocity of the material of the third acoustic matching layer 2c in order to secure or increase the directivity.

For example, the materials suitable for the third acoustic matching layer 2c are not limited to the rubber elastic materials but plastic materials are also usable. For example, materials in which filling materials are filled in polyethylene resin, polystyrene resin, polyimide resin, epoxy resin, or a material in which filling materials are filled in the epoxy resin described in Patent Document 2 may be used, and such materials have an acoustic velocity of about 1800 msec or more. When the third acoustic matching layer 2c is formed of such materials and is not divided similar to the configuration of the present embodiment, the directivity angle is narrowed, as is clearly understood from the result shown in FIG. 2. Therefore, when such materials are used, it is necessary to divide the third acoustic matching layer 2c in a manner similar to the piezoelectric elements 1 and the first and second acoustic matching layers 2a and 2b.

Moreover, although the third embodiment has been described for the case where the third acoustic matching layer 2c is formed of synthetic rubbers such as chloroprene rubber, ethylene-propylene copolymer rubber, and acrylonitrile-butadiene copolymer rubber, the same advantages can be obtained when the third acoustic matching layer 2c is mainly composed of other synthetic rubber materials such as butadiene rubber, isoprene rubber, styrene-butadiene copolymer rubber or acryl rubber.

Furthermore, although the third embodiment has been described for the case where the third acoustic matching layer 2c is formed of a rubber elastic material such as synthetic rubber, silicon rubber or urethane rubber, the same advantages can be obtained when the third acoustic matching layer 2c is formed of other elastomeric materials having a rubber elastic material.

Furthermore, although the third embodiment has been described for the case where the acoustic matching layer 2 has three layers, the same advantages can be obtained when the acoustic matching layer has four or more layers, and an acoustic matching layer disposed close to the subject is not divided but formed as a continuous body by using a rubber elastic material.

In addition, although the third embodiment has been described for the case where the piezoelectric elements are arranged in a one-dimensional manner, the same advantages can be obtained when the piezoelectric elements are arranged in a two-dimensional manner. Moreover, although the third embodiment has been described for the case where a plurality of piezoelectric elements is arranged, the same advantage of the broader bandwidth can be provided when the acoustic matching layer is configured to have three or more layers, and a rubber elastic material is used for the acoustic matching layer disposed close to the subject, even when the piezoelectric elements are not arranged but form a single body.

Furthermore, although the third embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Embodiment 4

Figure 6:
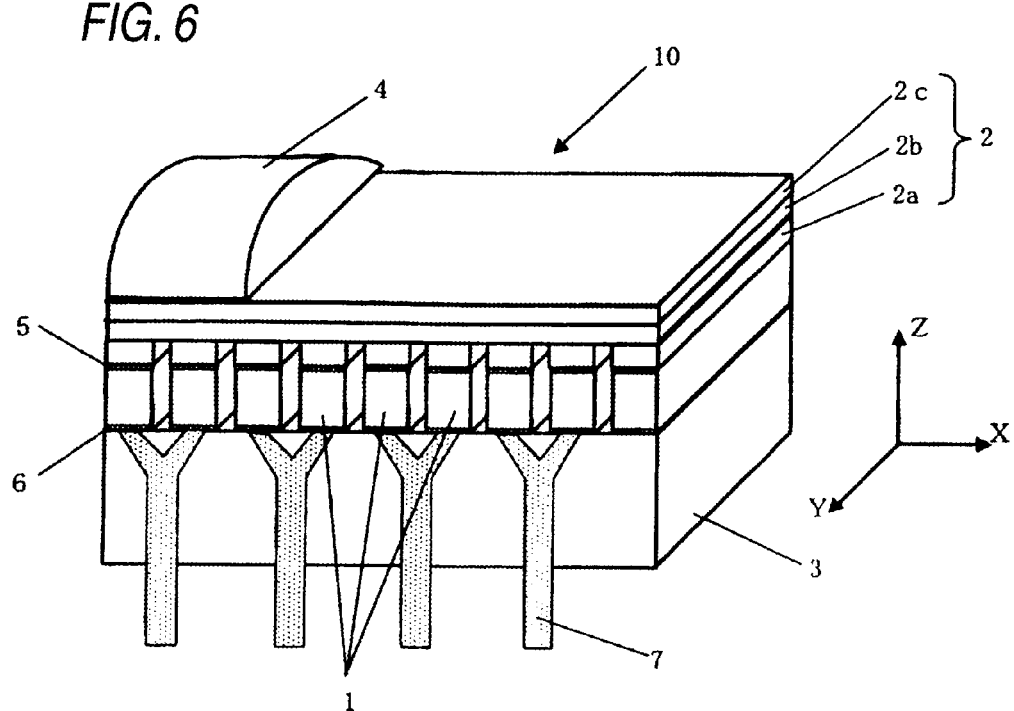
FIG. 6 is a schematic perspective view of an ultrasonic probe according to a fourth embodiment of the present invention.

Hereinafter, an ultrasonic probe according to a fourth embodiment of the present invention will be described with reference to the drawings. FIG. 6 is a partially schematic perspective view of an ultrasonic probe 10 according to the fourth embodiment.

The ultrasonic probe 10 is configured to include a plurality of piezoelectric elements 1, a three-layered acoustic matching layer 2 (2a, 2b and 2c) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2a, 2b and 2c), and an acoustic lens 4 provided, as necessary, on the acoustic matching layer 2 (2a, 2b and 2c). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

The electrodes 5 and 6 are electrically connected to an unillustrated ultrasonic diagnostic apparatus through a cable via an electric terminal 7, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the illustrated example, the piezoelectric elements 1 and a first acoustic matching layer 2a disposed close to the piezoelectric elements 1 are divided into individual ones, and materials, such as silicon rubber or urethane rubber, capable of reducing acoustic coupling are filled in portions corresponding to the division grooves. Moreover, a second acoustic matching layer 2b and a third acoustic matching layer 2c are provided as a non-divided, continuous film on an upper surface of the first acoustic matching layer 2a. In addition, an acoustic lens is provided as necessary by using materials such as silicon rubber.

In the ultrasonic probe 10 of a so-called electronic scanning type, having the plurality of piezoelectric elements 1 arranged therein, similar to the second and third embodiments, an important point in increasing the resolution of an ultrasonic image is how the directivity in the X direction of the piezoelectric elements 1 can be increased.

Although the second embodiment has been described for the case where the acoustic matching layer 2 has two layers, since the acoustic matching layer 2 is configured to have three layers, it is possible to further increase the bandwidth. However, when the acoustic matching layer is configured to have three or more layers, as described in Patent Documents 1 and 2, it was difficult to increase the directivity unless the acoustic matching layer 2 (2a, 2b and 2c) is divided in a manner similar to the piezoelectric elements 1.

This is because the acoustic matching layer 2 is divided by a slicing machine or the like in a manner similar to the piezoelectric elements 1, the thickness increases as the number of layers of the acoustic matching layer 2 increases, and because the number of materials of the layers to be divided increases, the division process is complicated, and thus, it is difficult to perform the division processing in a uniform and stable manner. The present embodiment relates to a configuration that solves such a problem to thereby provide a broader bandwidth and increase the directivity.

In the present embodiment, the acoustic matching layer is configured to have three layers, and as illustrated in FIG. 6, the piezoelectric elements 1 and the first acoustic matching layer 2a disposed close to the piezoelectric elements 1 are divided, and the second and third continuous acoustic matching layers 2b and 2c are provided on an upper surface of the first acoustic matching layer 2a.

As materials of the piezoelectric elements 1, PZT-based piezoelectric ceramic materials, PZN-PT-based or PMN-PT-based single-crystal piezoelectric materials, or a piezoelectric composite made of the materials and polymers are used. As materials of the first acoustic matching layer 2a, materials such as glass including single-crystal silicon, crystal or molten quartz, machinable ceramics, or graphite, having an acoustic impedance value ranging from 8 to 20 MRayls are used. As materials of the second acoustic matching layer 2b, materials such as a rubber elastic material in which fillers such as metal powder or oxide powder are filled, having an acoustic impedance value ranging from 3 to 8 MRayls are used.

Moreover, as materials of the third acoustic matching layer 2c, materials mainly composed of a rubber elastic material, such as silicon rubber, chloroprene rubber, ethylene-propylene copolymer rubber, acrylonitrile-butadiene copolymer rubber, and urethane rubber are used. The present embodiment is characterized in that neither the second acoustic matching layer 2b nor the third acoustic matching layer 2c is divided.

When the second acoustic matching layer 2b is not divided unlike the piezoelectric elements 1, the directivity is narrowed as described above and it is thus not desirable. However, even when the second acoustic matching layer is not divided, it does not cause any problem as long as the directivity is not narrowed. Moreover, as described in the second and third embodiments, the smaller number of constituent components, the easier the division process can be performed.

In order to use the configuration where the second and third acoustic matching layers 2b and 2c are not divided, as illustrated in FIG. 2 and described in the third embodiment, when the second acoustic matching layer 2b is formed of the same rubber elastic material as the third acoustic matching layer 2c and having an acoustic velocity value of 1650 msec or less, it is possible to obtain characteristics that the directivity is not narrowed even when the second acoustic matching layer 2b is not divided.

As materials of the second acoustic matching layer 2b having an acoustic impedance in the range of 3 to 8 MRayls and an acoustic velocity of 1650 m/sec or less, a material in which fillers of metal powder (average grain size of 1.2 µm) are filled in acrylonitrile-butadiene copolymer rubber at a ratio of 9:1 in terms of weight percent, having an acoustic impedance of 5.3 MRayls and an acoustic velocity of 1070 msec, which provides desired characteristic values as the second acoustic matching layer 2b is used.

In this way, by filling fillers having a large density such as oxides or metal powder such as tungsten, silver, iron or nickel in a material mainly composed of synthetic rubber-based elastic materials, it is possible to obtain a material having an acoustic impedance and an acoustic velocity needed by the second acoustic matching layer 2b.

In this way, it is possible to decrease the number of layers of the acoustic matching layer which is to be divided in a manner similar to the piezoelectric elements 1. Therefore, even when they are divided into narrow intervals (for example, 0.1 mm), the processing can be performed in a stable manner, and thus, it is possible to fabricate the ultrasonic probe in a uniform and precise manner without decreasing the directivity.

Moreover, the fourth embodiment has been described for the case where a material in which fillers of copper powder are filled in the acrylonitrile-butadiene copolymer rubber, which is synthetic rubber, is used for the second acoustic matching layer 2b, the same advantages can be obtained when a material composed of other fillers and synthetic material, such as chloroprene rubber, ethylene-propylene copolymer rubber, butadiene rubber, isoprene rubber, styrene-butadiene copolymer rubber or acryl rubber, silicon rubber, urethane rubber, or elastomeric materials is used.

Furthermore, although the fourth embodiment has been described for the case where the acoustic matching layer 2 has three layers, the same advantages can be obtained when the acoustic matching layer has four or more layers, and an acoustic matching layer disposed close to the subject is not divided but formed as a continuous body by using a rubber elastic material.

In addition, although the fourth embodiment has been described for the case where the piezoelectric elements are arranged in a one-dimensional manner, the same advantages can be obtained when the piezoelectric elements are arranged in a two-dimensional manner. Moreover, although the fourth embodiment has been described for the case where a plurality of piezoelectric elements is arranged, the same advantage of the broader bandwidth can be provided when the acoustic matching layer is configured to have three or more layers, and a rubber elastic material is used for the acoustic matching layer disposed close to the subject, even when the piezoelectric elements are not arranged but form a single body.

Furthermore, although the fourth embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Embodiment 5

Figure 7:
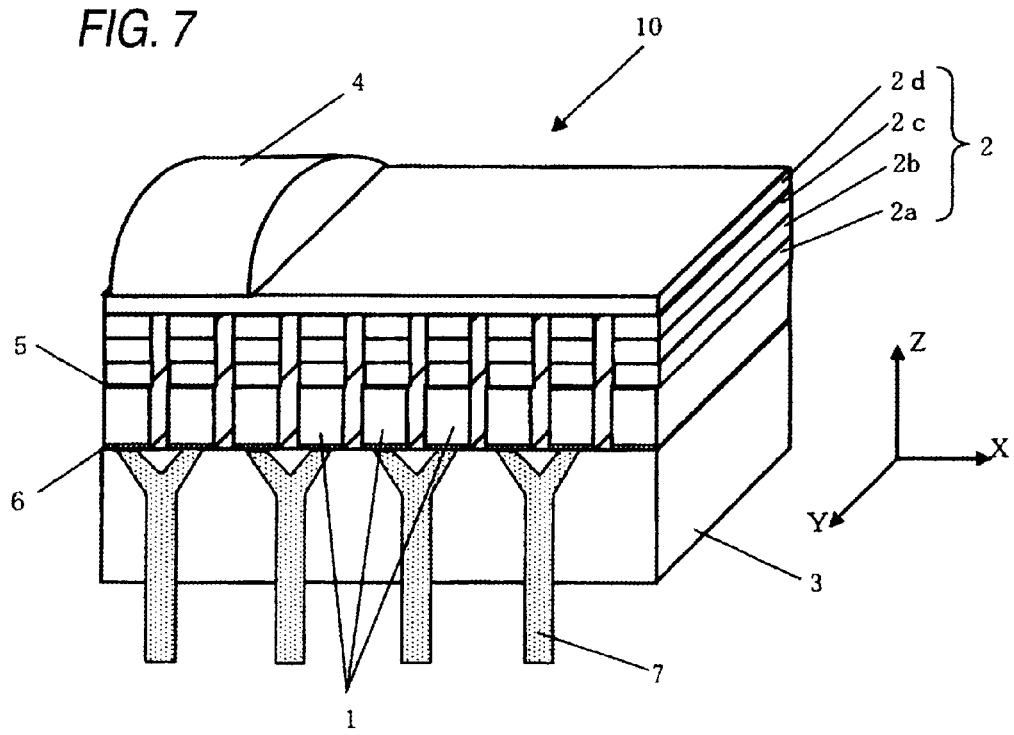
FIG. 7 is a schematic perspective view of an ultrasonic probe according to a fifth embodiment of the present invention.

Hereinafter, an ultrasonic probe according to a fifth embodiment of the present invention will be described with reference to the drawings. FIG. 7 is a partially schematic perspective view of an ultrasonic probe 10 according to the fifth embodiment.

The ultrasonic probe 10 is configured to include a plurality of piezoelectric elements 1, a four-layered acoustic matching layer 2 (2a, 2b, 2c and 2d) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2a, 2b, 2c and 2d), and an acoustic lens 4 provided, as necessary, on the acoustic matching layer 2 (2a, 2b, 2c and 2d). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

The electrodes 5 and 6 are electrically connected to an unillustrated ultrasonic diagnostic apparatus through a cable via an electric terminal 7, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the illustrated example, the piezoelectric elements 1, and acoustic matching layers 2a, 2b and 2c disposed close to the piezoelectric elements 1 are divided into individual ones, and materials, such as silicon rubber or urethane rubber, capable of reducing acoustic coupling are filled in portions corresponding to the division grooves. Moreover, another acoustic matching layer 2d is provided as one sheet of non-divided, continuous film on an upper surface of the acoustic matching layer 2c. In addition, an acoustic lens is provided as necessary by using materials such as silicon rubber.

In the ultrasonic probe 10 of a so-called electronic scanning type, having the plurality of piezoelectric elements 1 arranged therein, an important point in increasing the resolution of an ultrasonic image is how the directivity in the arrangement direction of the piezoelectric elements 1 can be increased.

Figure 12:
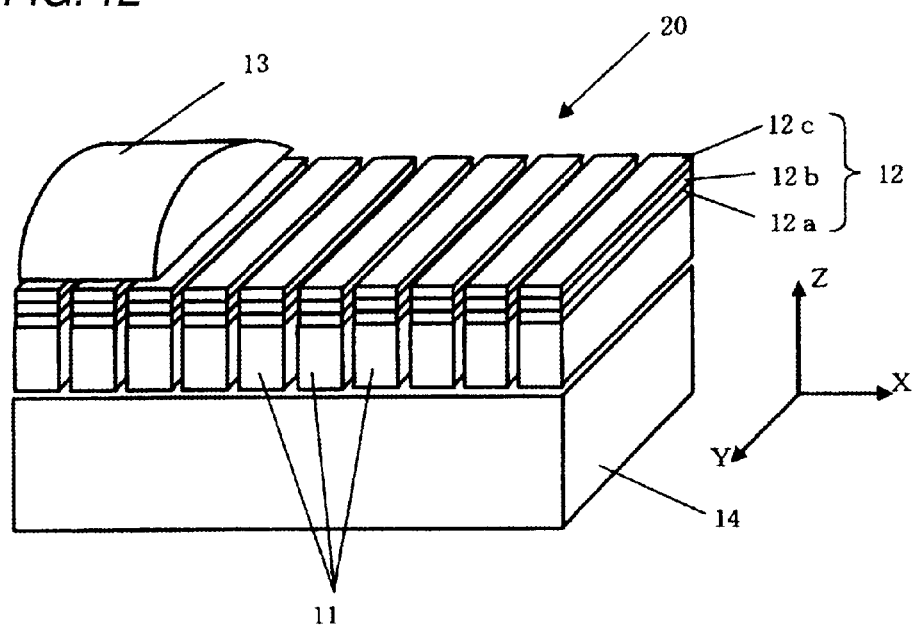
FIG. 12 is a schematic perspective view illustrating the configuration of an ultrasonic probe according to a prior art.

Since the acoustic matching layer 2 provided on the subject side of the piezoelectric elements 1 is configured to have a plurality of layers, it is possible to increase the bandwidth. However, when the acoustic matching layer is configured to have four or more layers, as illustrated in FIG. 12 (see Patent Documents 1 and 2), it was difficult to increase the directivity unless the three-layered acoustic matching layer 12 is divided in a manner similar to the piezoelectric elements 12.

This is because the acoustic matching layer 12 is divided by a slicing machine or the like in a manner similar to the piezoelectric elements 11, the thickness increases as the number of layers of the acoustic matching layer 12 is further increased, and because the number of materials of the layers to be divided increases, the division process is complicated, and thus, it is difficult to perform the division processing in a uniform and stable manner. The present embodiment relates to a configuration that solves such a problem to thereby provide a broader bandwidth and increase the directivity.

In the present embodiment, the acoustic matching layer is configured to have four layers, and as illustrated in FIG. 7, the piezoelectric elements 1 and first, second and third acoustic matching layers 2a, 2b and 2c disposed close to the piezoelectric elements 1 are divided, and a fourth continuous single-layered acoustic matching layer 2d is additionally provided on an upper surface of the third acoustic matching layer 2c.

As materials of the piezoelectric elements 1, PZT-based piezoelectric ceramic materials, PZN-PT-based or PMN-PT-based single-crystal piezoelectric materials, or a piezoelectric composite made of the materials and polymers are used. As materials of the first acoustic matching layer 2a, materials such as single-crystal silicon, crystal, tellurite glass, machinable ceramics, having an acoustic impedance smaller than that of the piezoelectric elements 1 are used. As materials of the second acoustic matching layer 2b, materials such as glass-based material typified by molten quartz, graphite or epoxy resin in which fillers such as metal or oxides are filled, having an acoustic impedance smaller than that of the first acoustic matching layer 2a are used. As materials of the third acoustic matching layer 2c, materials such as graphite or epoxy resin in which fillers such as metal or oxides are filled, having an acoustic impedance smaller than that of the second acoustic matching layer 2b are used.

Moreover, as materials of the fourth acoustic matching layer 2d, materials mainly composed of a rubber elastic material, such as silicon rubber, chloroprene rubber, ethylene-propylene copolymer rubber, acrylonitrile-butadiene copolymer rubber, and polyurethane rubber, having an acoustic impedance smaller than that of the third acoustic matching layer 2c are used. As is known, the respective acoustic matching layers 2 (2a, 2b, 2c and 2d) basically have a thickness basically corresponding to a ¼ wavelength of a using frequency.

The present embodiment is characterized in that the piezoelectric elements 1 and the first, second and third acoustic matching layers 2 (2a, 2b and 2c) are divided, and the fourth acoustic matching layer 2d of rubber elastic materials is provided on the upper surface of the third acoustic matching layer 2c in a one-layer state where the acoustic matching layer is not divided but connected, so that it is easy to process and the processing can be performed in a uniform and stable manner. The present embodiment is also characterized in that the resulting directivity is equal to or greater than that obtainable from the configuration where the division is performed up to the fourth acoustic matching layer 2d.

In order to obtain broader directivity with a configuration where the acoustic matching layer is not divided, as illustrated in FIG. 2 and described in the first embodiment, it is necessary to form the acoustic matching layer using a rubber elastic material having an acoustic velocity of 1650 msec or less. Therefore, materials having such characteristics are used for the fourth acoustic matching layer.

Moreover, although it has been described for the case where the fourth acoustic matching layer 2d is mainly composed of synthetic rubbers such as chloroprene rubber, ethylene-propylene copolymer rubber, and acrylonitrile-butadiene copolymer rubber, the same advantages can be obtained when the fourth acoustic matching layer 2d is mainly composed of other synthetic rubber materials such as butadiene rubber, isoprene rubber, styrene-butadiene copolymer rubber or acryl rubber.

Furthermore, although it has been described for the case where the fourth acoustic matching layer 2d is mainly composed of a rubber elastic material such as synthetic rubber, silicon rubber or urethane rubber, the same advantages can be obtained when the fourth acoustic matching layer 2d is formed of other elastomeric materials having a rubber elastic material.

In addition, although the fifth embodiment has been described for the case where the piezoelectric elements are arranged in a one-dimensional manner, the same advantages can be obtained when the piezoelectric elements are arranged in a two-dimensional manner. Moreover, although the fifth embodiment has been described for the case where a plurality of piezoelectric elements is arranged, the same advantage of the broader bandwidth can be provided when the acoustic matching layer is configured to have three or more layers, and a rubber elastic material is used for the acoustic matching layer disposed close to the subject, even when the piezoelectric elements are not arranged but form a single body.

Furthermore, although the fifth embodiment has been described for a so-called linear type in which a plurality of piezoelectric elements are arranged in an approximately straight line manner, the same advantages can be obtained for a convex type or a concave type in which a plurality of piezoelectric elements are arranged in a curved surface shape.

According to the configuration described above, since the acoustic velocity is defined by the rubber elastic material as the material of the fourth acoustic matching layer disposed on the subject side of the acoustic matching layer and the fourth acoustic matching layer is not divided, it is possible to provide broader frequency bandwidth and increase the directivity. Moreover, since it is not necessary to process and divide the fourth acoustic matching layer together with the piezoelectric elements, it is possible to eliminate difficulties in processing and provide a stable ultrasonic probe. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Embodiment 6

Hereinafter, an ultrasonic probe according to a sixth embodiment of the present invention will be described with reference to the drawings. FIG. 8 is a partially schematic perspective view of an ultrasonic probe 10 according to the sixth embodiment.

The ultrasonic probe 10 is configured to include a plurality of piezoelectric elements 1, a four-layered acoustic matching layer 2 (2a, 2b, 2c and 2d) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2a, 2b, 2c and 2d), and an acoustic lens 4 provided, as necessary, on the acoustic matching layer 2 (2a, 2b, 2c and 2d). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

The electrodes 5 and 6 are electrically connected to an unillustrated ultrasonic diagnostic apparatus through a cable via an electric terminal 7, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the illustrated example, the piezoelectric elements 1 and first and second acoustic matching layers 2a and 2b disposed close to the piezoelectric elements 1 are divided into individual ones, and materials, such as silicon rubber or urethane rubber, capable of reducing acoustic coupling are filled in portions corresponding to the division grooves.

Moreover, a third acoustic matching layer 2c and a fourth acoustic matching layer 2d are provided as a non-divided, continuous film on an upper surface of the second acoustic matching layer 2b. In addition, an acoustic lens is provided as necessary by using materials such as silicon rubber.

In the ultrasonic probe 10 of a so-called electronic scanning type, having the plurality of piezoelectric elements 1 arranged therein, similar to the first embodiment, an important point in increasing the resolution of an ultrasonic image is how the directivity in the X direction of the piezoelectric elements 1 can be increased.

In the present embodiment, the acoustic matching layer is configured to have four layers, and as illustrated in FIG. 8, the piezoelectric elements 1 and the first and second acoustic matching layers 2a and 2b disposed close to the piezoelectric elements 1 are divided, the third continuous acoustic matching layer 2c is provided on an upper surface of the second acoustic matching layer 2b, and the fourth continuous acoustic matching layer 2d is provided on an upper surface of the third acoustic matching layer 2c.

As materials of the piezoelectric elements 1, PZT-based piezoelectric ceramic materials, PZN-PT-based or PMN-PT-based single-crystal piezoelectric materials, or a piezoelectric composite made of the materials and polymers are used. As materials of the first acoustic matching layer 2a, materials such as single-crystal silicon, crystal, tellurite glass, machinable ceramics, having an acoustic impedance smaller than that of the piezoelectric elements 1 are used. As materials of the second acoustic matching layer 2b, materials such as glass-based material typified by molten quartz, graphite or epoxy resin in which fillers such as metal or oxides are filled, having an acoustic impedance smaller than that of the first acoustic matching layer 2a are used. As materials of the third acoustic matching layer 2c, rubber elastic materials having an acoustic impedance smaller than that of the second acoustic matching layer 2b and an acoustic velocity of 1650 msec or less are used.

Moreover, as materials of the fourth acoustic matching layer 2d, materials mainly composed of a rubber elastic material, such as silicon rubber, chloroprene rubber, ethylene-propylene copolymer rubber, acrylonitrile-butadiene copolymer rubber, and urethane rubber, having an acoustic impedance smaller than that of the third acoustic matching layer 2c are used. As is known, the respective acoustic matching layers 2 (2a, 2b, 2c and 2d) basically have a thickness basically corresponding to a ¼ wavelength of a using frequency.

The present embodiment is characterized in that the piezoelectric elements 1 and the first and second acoustic matching layers 2 (2a and 2b) are divided, and the third acoustic matching layer 2c of rubber elastic materials is provided on the upper surface of the second acoustic matching layer 2b in a one-layer state where the acoustic matching layer is not divided but connected, and moreover, the fourth acoustic matching layer 2d is provided on the upper surface of the third acoustic matching layer in a one-layer state where it is not divided but connected in a manner similar to the third acoustic matching layer 2c, so that it is easy to process and the processing can be performed in a uniform and stable manner. The present embodiment is also characterized in that the resulting directivity is equal to or greater than that obtainable from the configuration where the division is performed up to the third and fourth acoustic matching layers 2c and 2d.

When the third acoustic matching layer 2c is not divided unlike the piezoelectric elements 1, the directivity is narrowed as described above and it is thus not desirable. However, even when the second acoustic matching layer is not divided, it does not cause any problem as long as the directivity is not narrowed. Moreover, as described in the first embodiment, the smaller number of constituent components, the easier the division process can be performed.

In order to use the configuration where the third and fourth acoustic matching layers 2c and 2d are not divided, as illustrated in FIG. 2 and described in the first embodiment, when the third acoustic matching layer 2c is formed of the same rubber elastic material as the fourth acoustic matching layer 2d and having an acoustic velocity of 1650 msec or less, it is possible to obtain characteristics that the directivity is not narrowed even when the third acoustic matching layer 2c is not divided.

As materials of the third acoustic matching layer 2c having an acoustic impedance intermediate between those of the second and fourth acoustic matching layers 2b and 2d and an acoustic velocity of 1650 msec or less, a material in which fillers of metal powder (average grain size of 1.2 μm) are filled in acrylonitrile-butadiene copolymer rubber at a ratio of 9:1 in terms of weight percent, having an acoustic impedance of 5.3 MRayls and an acoustic velocity of 1070 msec, which provides desired characteristics as the third acoustic matching layer 2c is used.

In this way, by filling fillers having a large density such as oxides or metal powder such as tungsten, silver, iron or nickel in a material mainly composed of synthetic rubber-based elastic materials, it is possible to obtain a material having an acoustic impedance and an acoustic velocity needed by the third acoustic matching layer 2c.

In this way, it is possible to decrease the number of layers of the acoustic matching layer which is to be divided in a manner similar to the piezoelectric elements 1. Therefore, even when they are divided into narrow intervals (for example, 0.1 mm), the processing can be performed in a stable manner, and thus, it is possible to fabricate the ultrasonic probe in a uniform and precise manner without decreasing the directivity.

Moreover, the sixth embodiment has been described for the case where a material in which fillers of copper powder are filled in the acrylonitrile-butadiene copolymer rubber, which is synthetic rubber, is used for the third acoustic matching layer 2c, the same advantages can be obtained when a material composed of other fillers and synthetic material, such as chloroprene rubber, ethylene-propylene copolymer rubber, butadiene rubber, isoprene rubber, styrene-butadiene copolymer rubber or acryl rubber, silicon rubber, urethane rubber, or elastomeric materials is used.

Furthermore, although the sixth embodiment has been described for the case where the acoustic matching layer 2 has four layers, the same advantages can be obtained when the acoustic matching layer has two layers or five or more layers, and an acoustic matching layer disposed close to the subject is not divided but formed as a continuous body by using a rubber elastic material.

In addition, although the sixth embodiment has been described for the case where the piezoelectric elements are arranged in a one-dimensional manner, the same advantages can be obtained when the piezoelectric elements are arranged in a two-dimensional manner. Moreover, although the sixth embodiment has been described for the case where a plurality of piezoelectric elements are arranged, the same advantage of the broader bandwidth can be provided when the acoustic matching layer is configured to have three or more layers, and a rubber elastic material is used for the acoustic matching layer disposed close to the subject, even when the piezoelectric elements are not arranged but form a single body.

Furthermore, although the sixth embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Embodiment 7

Figure 9B:
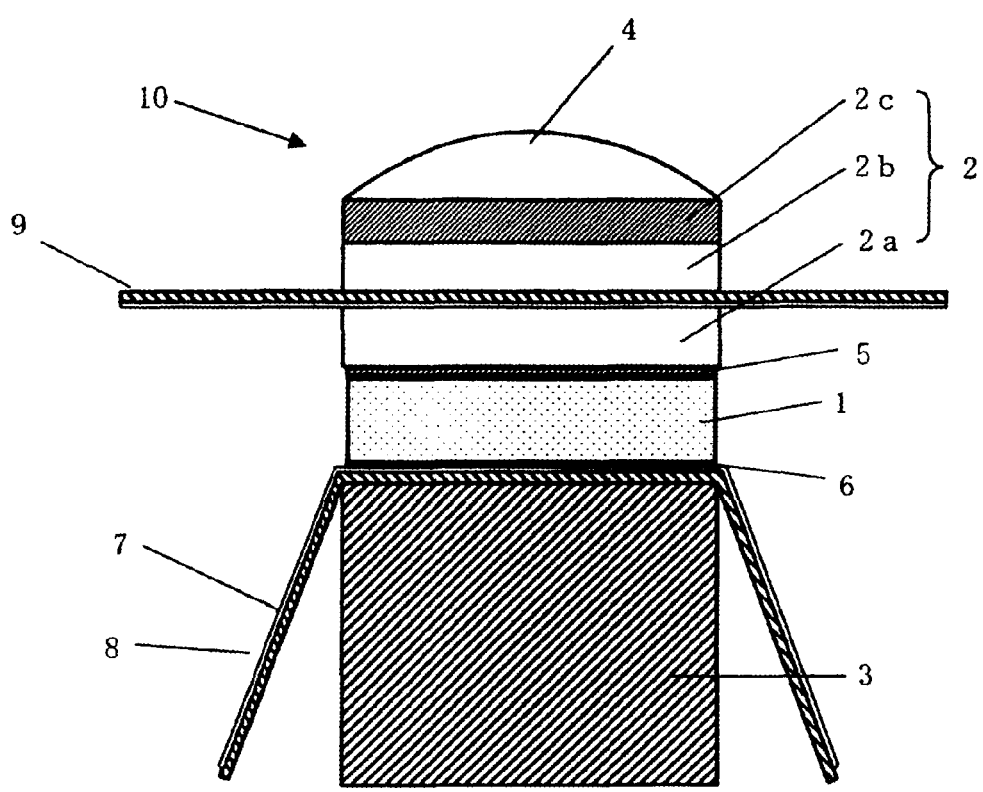
FIG. 9B is a schematic sectional view of the ultrasonic probe according to the first embodiment of the present invention.

Hereinafter, an ultrasonic probe according to a seventh embodiment of the present invention will be described with reference to the drawings. FIG. 9A is a partially schematic perspective view of an ultrasonic probe 10 according to the seventh embodiment, and FIG. 9B is a schematic sectional view as viewed from the X direction in FIG. 9A.

The ultrasonic probe 10 is configured to include a plurality of piezoelectric elements 1, a three-layered acoustic matching layer 2 (2a, 2b and 2c) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2a, 2b and 2c), and an acoustic lens 4 provided, as necessary, on the acoustic matching layer 2 (2a, 2b and 2c). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

Further detailed description will be provided below. Between the signal electrode 6 provided on the piezoelectric elements 1 made of materials such as PZT-based piezoelectric ceramic materials, PZN-PT-based or PMN-PT-based single-crystal piezoelectric materials, or a piezoelectric composite composed of the materials and polymers, and the backing load member 3, a film 8 (first polymer film), in which a metal film of copper or the like is provided on a polymer film of polyimide or the like, is provided, the electric terminal 7 of the metal film of the film 8 is in contact with the signal electrode 6, and the polymer film is in contact with the backing load member 3.

Meanwhile, on the side of the ground electrode 5 provided on the surface of the piezoelectric elements 1, a first acoustic matching layer 2a, which is a conductor such as graphite (if it is an insulating material, the insulator is plated with metal to form a conductor). Moreover, a film 9 (second polymer film), in which a metal film of copper (having a thickness of 5 μm or less so that the characteristics are not influenced greatly) is provided on a polymer film of polyimide or the like, is provided on an upper surface of the first acoustic matching layer 2a, and the first acoustic matching layer 2a, which is a conductor, and the film 9 are in contact with each other.

Further, a second acoustic matching layer 2b formed of materials, such as graphite or epoxy resin in which fillers such as metal or oxides are filled, is provided on an upper surface of the polymer film of the film 9. Moreover, when the first acoustic matching layer 2a is formed of an insulating material, since a conductor can be formed by means of plating the entire surroundings of the insulator, it is not always necessary to form the first acoustic matching layer 2a using a conductor. Furthermore, it does not matter whether the second acoustic matching layer 2b is formed of an insulator or a conductor.

After the configuration described above is formed, a portion of the backing load member 3, the film 8, the piezoelectric elements 1, the first acoustic matching layer 2a, the film 9, and the second acoustic matching layer 2b are processed and divided by means of a slicing machine or the like. In portions corresponding to the division grooves, materials such as silicon rubber or urethane rubber, capable of reducing acoustic coupling are filled, and a third acoustic matching layer 2c is provided on an upper surface of the second acoustic matching layer 2b and the filled portions of the division grooves.

The third acoustic matching layer 2c is provided in a state where it is not divided but connected, as illustrated in the drawing. Moreover, as materials of the third acoustic matching layer 2c, materials mainly composed of a rubber elastic material, such as silicon rubber, chloroprene rubber, ethylene-propylene copolymer rubber, acrylonitrile-butadiene copolymer rubber, and urethane rubber are used. Furthermore, an acoustic lens 4 formed of materials such as silicon rubber is provided, as necessary, on an upper surface of the third acoustic matching layer 2c.

The signal electrode 6 is electrically connected to an unillustrated ultrasonic diagnostic apparatus through a cable via the metal film of the electric terminal 7 of the film 8, and the ground electrode 5 is electrically connected to the ultrasonic diagnostic apparatus through a cable via the first acoustic matching layer 2a and the conductor of the metal film of the film 9, so that a regular pulse voltage generated by the ultrasonic probe is applied to the piezoelectric elements 1, and an echo reception signal converted into an electric signal by the piezoelectric elements 1 is transmitted to a body of the ultrasonic diagnostic apparatus.

In the ultrasonic probe 10 of a so-called electronic scanning type, having the plurality of piezoelectric elements 1 arranged therein, an important point in increasing the resolution of an ultrasonic image is how the directivity in the arrangement direction of the piezoelectric elements 1 can be increased.

Meanwhile, since the piezoelectric elements 1 has an acoustic impedance of about 30 MRayls and the subject has an acoustic impedance of about 1.54 MRayls and thus the difference thereof is larger, an acoustic mismatching occurs; therefore, the frequency bandwidth is narrowed. In order to obviate such an acoustic mismatching, when a material having an acoustic impedance intermediate between those of the piezoelectric elements 1 and the subject is used for the acoustic matching layer, it is possible to increase the frequency bandwidth.

When the number of steps wherein the acoustic impedance of the acoustic matching layer is gradually approached toward that of the subject from that of the piezoelectric elements is increased, it is possible to further increase the frequency bandwidth. Therefore, when the number of layers of the acoustic matching layer is increased from one to two, or from two to three, and so on, a broader bandwidth can be provided.

In addition, by decreasing the number of layers of the acoustic matching layer which is to be divided in a manner similar to the piezoelectric elements 1, even when they are divided into narrow intervals (for example, 0.1 mm), the processing can be performed in a stable manner, and thus, it is possible to fabricate the ultrasonic probe in a uniform and precise manner without decreasing the directivity.

For example, an angle of the directivity when the piezoelectric elements 1 having a frequency of 3.5 MHz are divided into intervals of 0.38 mm corresponding to the gaps of the divided piezoelectric elements 1 (a state where two parts divided into intervals of 0.19 mm are electrically coupled), as defined at a level of −6 dB, corresponds to a directivity angle of about 23 degrees for a configuration type where the acoustic matching layer 2 is divided together with the piezoelectric elements 1. Furthermore, it was configured such that silicon rubber materials are filled in the division grooves of the piezoelectric elements 1 and the first and second acoustic matching layers 2a and 2b.

In a configuration type where the piezoelectric elements 1 are divided with the same specifications by the above-mentioned method, and among the three-layered acoustic matching layer, the first and second acoustic matching layers 2a and 2b disposed close to the piezoelectric elements 1 are divided in a manner similar to the piezoelectric elements 1, while the third acoustic matching layer is not divided, the directivity characteristics of ultrasonic waves in the arrangement direction of the piezoelectric elements 1 were measured in a state where a plurality of third acoustic matching layers 2 disposed close to the subject is prepared, respectively formed of silicon rubber (hardness: 76 on shore A hardness, acoustic velocity: 915 msec, acoustic impedance: 2.1 MRayls), chloroprene rubber (hardness: 70 on shore A hardness, acoustic velocity: 1630 msec, acoustic impedance: 2.16 MRayls), ethylene-propylene copolymer rubber (hardness: 65 on shore A hardness, acoustic velocity: 1480 msec, acoustic impedance: 1.94 MRayls), acrylonitrile-butadiene copolymer rubber (hardness: 60 on shore A hardness, acoustic velocity: 1640 msec, acoustic impedance: 1.97 MRayls), and urethane rubber (hardness: 78 on shore A hardness, acoustic velocity: 1850 msec, acoustic impedance: 1.98 MRayls), and the respective acoustic matching layers 2 are placed on the surface of the piezoelectric elements 1, and an acoustic lens formed of silicon rubber is provided on the upper surface of the acoustic matching layer 2.

As a result of the measurement, it can be concluded that the directivity characteristics changed depending on the materials of the third acoustic matching layer 2. Moreover, in the division grooves (at this time, the division groove has a width of about 0.03 mm) of the divided piezoelectric elements 1 and the first and second acoustic matching layers, silicon rubber materials were filled in a manner similar to the configuration where the division is performed up to the second acoustic matching layer 2.

Moreover, as a material other than the urethane rubber as mentioned above, a material in which an arbitrary amount of fillers such as alumina, carbon or calcium carbonate is filled in order to adjust an acoustic impedance was used.

The difference in the directivity characteristics was neither correlated with nor influenced by the hardness, the acoustic impedance, and the like of the materials. However, the acoustic velocity characteristics of the materials of the third acoustic matching layers 2 had influence on, that is, was correlated with, the directivity characteristics, and showed good correlation.

The relationship between the directivity angle measured at a level of −6 dB using a frequency of 3.5 MHz and an acoustic velocity of the material is illustrated in FIG. 2 (described above). As illustrated in FIG. 2, it showed good correlation with an acoustic velocity, and a correlation coefficient was 0.86. In this respect, in the configuration where the acoustic matching layer 2 disposed close to the subject is not divided, it can be concluded that it is necessary to focus on the acoustic velocity in order to increase the directivity. The directivity angles when the respective materials were used for the acoustic matching layer 2 are as follows.

The respective directivity angles were 25 degrees for the silicon rubber, 23.5 degrees for the chloroprene rubber, 23.5 degrees for the ethylene-propylene copolymer rubber, 22.9 degrees for the acrylonitrile-butadiene copolymer rubber, and 20 degrees for the urethane rubber. Moreover, it is considered that the measurement result has a deviation of about ±0.5 degrees.

Therefore, even when the entire multi-layered acoustic matching layers are not divided unlike the piezoelectric elements 1, in order to obtain directivity characteristics equal to or better than that of the configuration where the acoustic matching layers are divided, it can be concluded that it is necessary to regulate the acoustic velocity of the acoustic matching layer, and rubber elastic materials can provide an acoustic velocity of 1650 msec or less.

Based on the results, in the present embodiment, the acoustic matching layer 2 is configured to have three layers, and the third acoustic matching layer 2c disposed close to the subject is formed of rubber elastic materials having an acoustic velocity of 1650 m/sec or less and is not divided, so that the directivity can be increased.

Moreover, since the acoustic matching layer 2 is configured to have three layers, it is possible to provide a broader bandwidth. When the directivity angles were compared with the directivity angle of the prior art configuration where the acoustic matching layer 2 is divided together with the piezoelectric elements 1, in order to obtain a directivity angle approximately equal to the directivity angle of the prior art configuration, it is necessary to form the acoustic matching layer 2 using a material having an acoustic velocity in the vicinity of 1650 msec. Moreover, in order to increase the directivity, it can be concluded from the result illustrated in FIG. 2 that it is necessary to use a material having an acoustic velocity of 1650 msec or less, for example, a material such as silicon rubber.

Moreover, in the case of the urethane rubber which showed a narrow directivity angle, since among urethane rubbers, some kinds of products (for example, medium-size urethane resin of a grade UE-644, manufactured by SANYU REC Co., Ltd. has an acoustic velocity of 1580 msec and an acoustic impedance of 2.1 MRayls) have an acoustic velocity in the vicinity of 1650 msec or less, it cannot be said that the urethane rubber narrows the directivity angle, and the directivity angle is determined by an acoustic velocity. Therefore, when materials having an acoustic velocity of 1650 msec or less are selected, the materials are basically narrowed down to the rubber elastic materials.

As described above, in the configuration where the acoustic matching layer 2 is not divided unlike the piezoelectric elements 1 but is provided as one sheet of continuous film, in order to secure or increase the directivity, it can be concluded that it is necessary to focus on an acoustic velocity of the material of the acoustic matching layer 2.

For example, a material of the third acoustic matching layer 2c, having an acoustic impedance in the vicinity of 2 MRayls as the materials mentioned above is not limited to the rubber elastic materials but plastic materials are also usable. For example, materials in which filling materials are filled in polyethylene resin, polystyrene resin, or the epoxy resin described in Patent Document 2 may be used, and such materials have an acoustic velocity of about 1800 msec or more. When the third acoustic matching layer 2c is formed of such materials and is not divided similar to the configuration of the present embodiment, the directivity is narrowed, as is clearly understood from the relationship shown in FIG. 2. Therefore, when such materials are used, it is necessary to configure such that the acoustic matching layer 2 is divided in a manner similar to the piezoelectric elements 1, so that the directivity is increased.

In addition, although the metal film of the film 9 provided between the first and second acoustic matching layers is formed of a material such as copper, since copper has a high acoustic velocity of 4700 msec and can be formed to a thickness of 5 μm or less, it does not have much influence on the frequency characteristics and no further consideration is needed. However, the polymer film of the film 9 is formed of a material such as polyimide.

The polymer film has an acoustic impedance of about 3 MRayls, smaller than those of the first and second acoustic matching layers 2a and 2b, and has a low acoustic velocity of 2200 msec; therefore, a thickness thereof has influence on the frequency characteristics. In the configuration where three acoustic matching layers are provided, the acoustic impedances of the respective acoustic matching layers are typically set such that the first acoustic matching layer 2a has an acoustic impedance in the range of 8 to 20 MRayls, the second acoustic matching layer 2b has an acoustic impedance in the range of 3 to 8 MRayls, and the third acoustic matching layer 2c has an acoustic impedance in the range of 1.7 to 2.4 MRayls.

Figure 10:
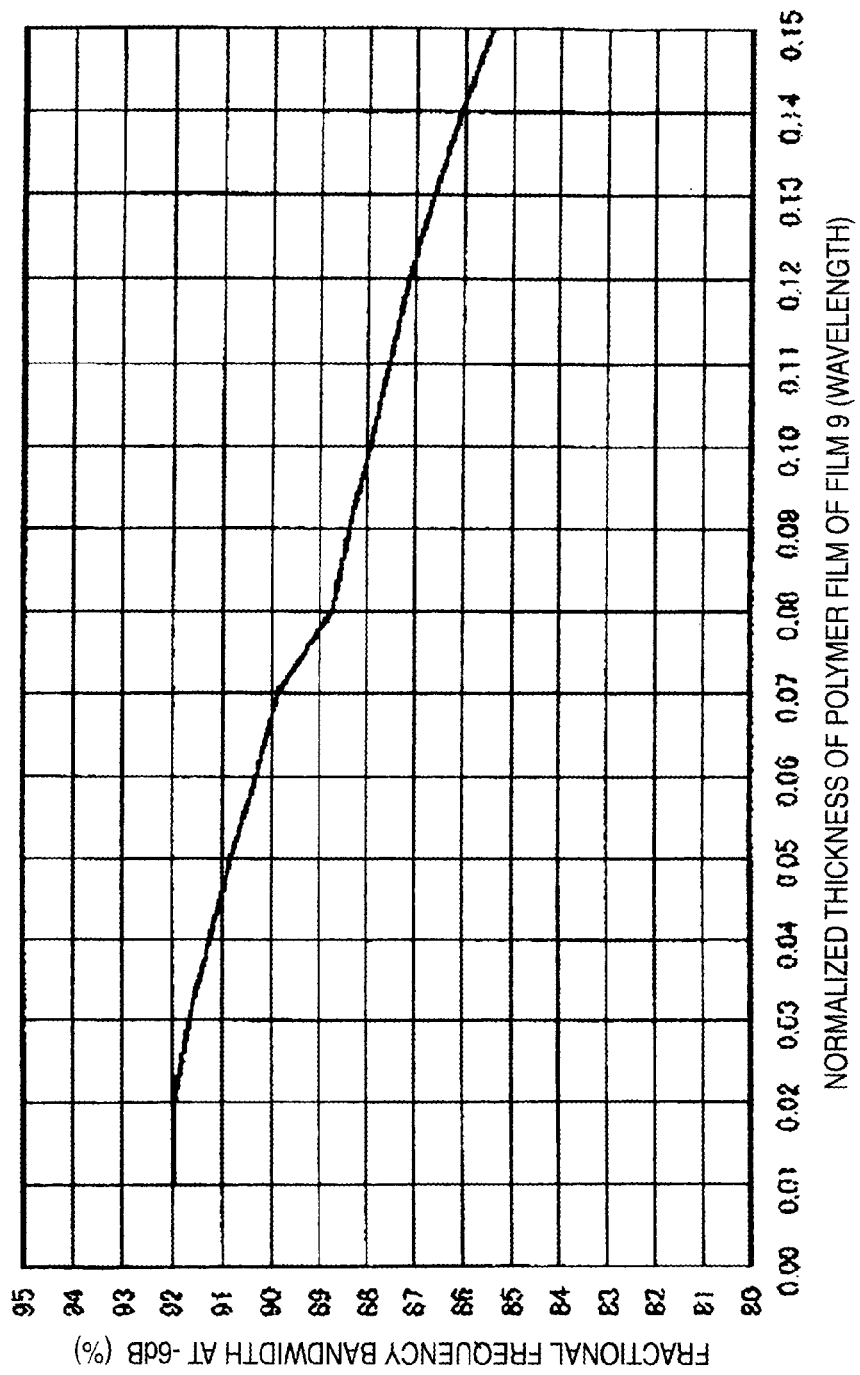
FIG. 10 is a diagram illustrating the relationship between a thickness and a fractional bandwidth of a polymer film.

In the present embodiment, when the first acoustic matching layer is formed of a material having an acoustic impedance of 10 MRayls, the second acoustic matching layer is formed of a material having an acoustic impedance of 4 MRayls, the polymer film of the film 9 is formed of polyimide, so that the acoustic matching layer has three layers, a calculation result of a fractional bandwidth of the frequency characteristics at −6 dB with a frequency of 3.5 MHz is illustrated in FIG. 10.

In FIG. 10, a horizontal axis represents a thickness of the polymer film of polyimide as the film 8, normalized to wavelength, and the vertical axis represents a fractional bandwidth (bandwidth/central frequency) at −6 dB.

As will be clearly understood from FIG. 10, since the acoustic matching layer has three layers, it was possible to obtain broad bandwidth characteristics having a fractional bandwidth of 90 percents or more, and the fractional bandwidth showed a tendency to decrease as the thickness of the film 9 increases. When it is consider that the acoustic matching layer is configured to have three layers in order to provide a broader bandwidth, it is necessary to secure a fractional bandwidth of at least 90 percent or more. Here, when the fractional bandwidth is set to 90 percent or more, the thickness of the polymer film of the film 9 has to be set to 0.07 wavelength or less. In this case, since the frequency is 3.5 MHz and polyimide is used for the polymer film of the film 9, the thickness of 0.07 wavelength or less corresponds to 44 µm or less.

As described above, when a layer is disposed between the acoustic matching layers and an acoustic impedance of the layer is outside the range of the acoustic impedance of the acoustic matching layers, it is necessary to set the thickness or the like so that the frequency characteristics are not influenced much; in this case, the influence was clearly eliminated by setting the thickness to 0.07 wavelength or less.

In this way, since a rubber elastic material is used for the third acoustic matching layer disposed close to the subject side of the acoustic matching layers, it is possible to provide broader frequency bandwidth and increase the directivity. Moreover, since it is not necessary to process and divide the third acoustic matching layer together with the piezoelectric elements, it is possible to eliminate difficulties in processing. Furthermore, since the electric terminal is drawn from the conductor provided to the film, it is possible to obtain a stable and high-quality ultrasonic probe. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Moreover, although the seventh embodiment has been described for the case where the third acoustic matching layer 2c is formed of synthetic rubbers such as chloroprene rubber, ethylene-propylene copolymer rubber, and acrylonitrile-butadiene copolymer rubber, the same advantages can be obtained when the third acoustic matching layer 2c is mainly composed of other synthetic rubber materials such as butadiene rubber, isoprene rubber, styrene-butadiene copolymer rubber or acryl rubber.

Furthermore, although the seventh embodiment has been described for the case where the third acoustic matching layer 2c is formed of a rubber elastic material such as synthetic rubber, silicon rubber or urethane rubber, the same advantages can be obtained when the third acoustic matching layer 2c is formed of other elastomeric materials having a rubber elastic material.

Moreover, although the seventh embodiment has been described for the case where a plurality of piezoelectric elements is arranged, the same advantage of the broader bandwidth can be provided when the acoustic matching layer is configured to have three or more layers, and a rubber elastic material is used for the acoustic matching layer disposed close to the subject, even when the piezoelectric elements are not arranged but form a single body.

Furthermore, although the seventh embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Embodiment 8

Figure 11:
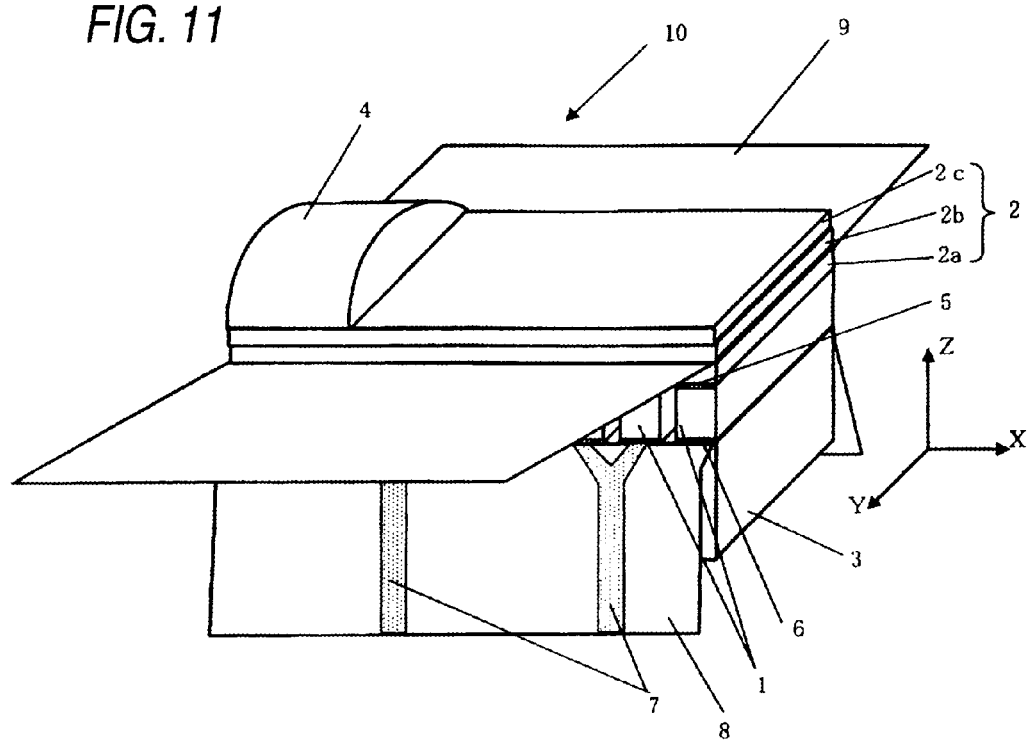
FIG. 11 is a schematic perspective view of the ultrasonic probe according to the second embodiment of the present invention.

Hereinafter, an ultrasonic probe according to an eighth embodiment of the present invention will be described with reference to the drawings. FIG. 11 is a partially schematic perspective view of an ultrasonic probe 10 according to the eighth embodiment.

The ultrasonic probe 10 is configured to include a plurality of piezoelectric elements 1, a three-layered acoustic matching layer 2 (2a, 2b and 2c) provided on a front surface in the thickness direction at a subject side (upper side in the drawing) so as to correspond to the respective piezoelectric elements 1, a backing load member 3 provided, as necessary, on a rear surface (lower surface in the drawing) in the thickness direction of the piezoelectric elements 1 at a side opposite to the acoustic matching layer 2 (2a, 2b and 2c), and an acoustic lens 4 provided, as necessary, on the acoustic matching layer 2 (2a, 2b and 2c). The respective functions of the above-mentioned components are the same as those of the components described in the prior art.

A ground electrode 5 and a signal electrode 6 are provided on the front surface and the rear surface in the thickness direction Z of the piezoelectric elements 1, respectively. The electrodes 5 and 6 are formed on the front surface and the rear surface of the piezoelectric elements 1, respectively, by means of deposition or sputtering of gold and silver or silver printing.

Further detailed description will be provided below. Between the signal electrode 6 provided on the piezoelectric elements 1 made of materials such as PZT-based piezoelectric ceramic materials, PZN-PT-based or PMN-PT-based single-crystal piezoelectric materials, or a piezoelectric composite composed of the materials and polymers, and the backing load member 3, a film 8 (first polymer film), in which a metal film of copper or the like is provided on a polymer film of polyimide or the like, is provided, the electric terminal 7 of the metal film of the film 8 is in contact with the signal electrode 6, and the polymer film is in contact with the backing load member 3.

Meanwhile, on the side of the ground electrode 5 provided on the surface of the piezoelectric elements 1, a first acoustic matching layer 2a, which is a conductor such as graphite (if it is an insulating material, the insulator is plated with metal to form a conductor). After the configuration described above is formed, a portion of the backing load member 3, the film 8, the piezoelectric elements 1, and the first acoustic matching layer 2a are processed and divided by means of a slicing machine or the like.

In portions corresponding to the division grooves, materials such as silicon rubber or urethane rubber, capable of reducing acoustic coupling are filled, and a film 9 (second polymer film) having a polymer film and a conductor of a metal film having a function of an electric terminal that is drawn from the ground electrode 5 via the first acoustic matching layer is provided on an upper surface of the first acoustic matching layer 2a and the filled portions of the division grooves. Moreover, a second acoustic matching layer 2b is provided on an upper surface of the film 9, and a third acoustic matching layer 2c is provided on an upper surface (at a subject side) of the second acoustic matching layer 2b.

The film 9 and the second and third acoustic matching layers 2b and 2c are provided in a state where they are not divided but connected, as illustrated in the drawing. Moreover, as materials of the second and third acoustic matching layers 2b and 2c, materials mainly composed of a rubber elastic material, such as silicon rubber, chloroprene rubber, ethylene-propylene copolymer rubber, acrylonitrile-butadiene copolymer rubber, and urethane rubber are used. Furthermore, an acoustic lens 4 formed of materials such as silicon rubber is provided, as necessary, on an upper surface of the third acoustic matching layer 2c.

The present embodiment is characterized in that neither the second acoustic matching layer 2b nor the third acoustic matching layer 2c is divided. When the second acoustic matching layer 2b is not divided unlike the piezoelectric elements 1, the directivity is narrowed as described above and it is thus not desirable. However, even when the second acoustic matching layer is not divided, it does not cause any problem as long as the directivity is not narrowed. Moreover, as described in the seventh embodiment, the smaller number of constituent components, the easier the division process can be performed.

In order to use the configuration where the second and third acoustic matching layers 2b and 2c are not divided so that the directivity is not narrowed, as illustrated in FIG. 2 and described in the seventh embodiment, it is necessary that the second acoustic matching layer 2b is formed of the same rubber elastic material as the third acoustic matching layer 2c and having an acoustic velocity of 1650 m/sec or less.

As materials of the second acoustic matching layer 2b having an acoustic impedance in the range of 3 to 8 MRayls and an acoustic velocity of 1650 m/sec or less, a material in which fillers of metal powder (average grain size of 1.2 μm) are filled in acrylonitrile-butadiene copolymer rubber at a ratio of 9:1 in terms of weight percent, having an acoustic impedance of 5.3 MRayls and an acoustic velocity of 1070 msec, which provides desired characteristics as the second acoustic matching layer 2b is used.

In this way, by filling fillers having a large density such as oxides or metal powder such as tungsten, silver, iron or nickel in a material mainly composed of synthetic rubber-based elastic materials, it is possible to obtain a material having an acoustic impedance and an acoustic velocity needed by the second acoustic matching layer 2b.

In addition, the thickness of the polymer film of the film 9 provided between the first acoustic matching layer and the second acoustic matching layer 2b is set to 0.07 wavelength or less, similar to the first embodiment.

Moreover, although the eighth embodiment has been described for the case where the second and third acoustic matching layers 2b and 2c are formed of synthetic rubbers such as chloroprene rubber, ethylene-propylene copolymer rubber, and acrylonitrile-butadiene copolymer rubber, the same advantages can be obtained when the second and third acoustic matching layers 2b and 2c are mainly composed of other synthetic rubber materials such as butadiene rubber, isoprene rubber, styrene-butadiene copolymer rubber or acryl rubber.

In this way, since a rubber elastic material is used for the second and third acoustic matching layers, it is possible to provide broader frequency bandwidth and increase the directivity. Moreover, since it is not necessary to process and divide the second and third acoustic matching layers together with the piezoelectric elements, it is possible to eliminate difficulties in processing. Furthermore, since the electric terminal is drawn from the conductor provided to the film, it is possible to obtain a stable and high-quality ultrasonic probe. Accordingly, phase control can be freely performed by using a greater number of piezoelectric elements, and thus an ultrasonic beam can be condensed narrow. Furthermore, since the ultrasonic beam can be deflected, it is possible to provide an ultrasonic probe capable providing a high-resolution ultrasonic image.

Furthermore, although the eighth embodiment has been described for the case where the second and third acoustic matching layers 2b and 2c are formed of a rubber elastic material such as synthetic rubber, silicon rubber or urethane rubber, the same advantages can be obtained when the second and third acoustic matching layers 2b and 2c are formed of other elastomeric materials having a rubber elastic material.

In addition, although the eighth embodiment has been described for the case where the first acoustic matching layer is divided together with the piezoelectric elements 1, the same advantages can be provided when the first acoustic matching layer 2a and the film 9 are divided together with the piezoelectric elements 1, and the second and third acoustic matching layers 2b and 2c are formed thereon having a rubber elastic material having an acoustic velocity of 1650 m/sec or less.

Furthermore, although the eighth embodiment has been described for a so-called linear type in which a plurality of piezoelectric elements is arranged in an approximately straight line manner, the same advantages can be obtained for a convex type or a concave type in which a plurality of piezoelectric elements is arranged in a curved surface shape.

Although the invention has been described in detail with reference to specific embodiments, it will be apparent to those skilled in the art that various modifications and variations can be made to the above-described embodiments of the present invention without departing from the spirit or scope of the invention.

This application is based upon and claims the benefit of priority from the prior Japanese Patent Application Nos. 2006-023169 filed on Jan. 31, 2006, and 2006-023170 filed on Jan. 31, 2006, the entire contents of which are incorporated herein by reference.

INDUSTRIAL APPLICABILITY

The ultrasonic probe according to the present invention can be applied to various medical fields in which an ultrasonic diagnosis is conducted on a subject such as a human body and to an industrial field.

The invention claimed is:
1. An ultrasonic probe, comprising:
a plurality of piezoelectric elements which are separated from each other by a gap; and
an acoustic matching layer which extends as a continuous, undivided single layer over a surface of each of the plurality of piezoelectric elements,
wherein an acoustic impedance of the acoustic matching layer is smaller than an acoustic impedance of the plurality of piezoelectric elements and larger than an acoustic impedance of a subject, and
wherein an acoustic velocity of the acoustic matching layer has a value of 1650 m/sec or less.
2. The ultrasonic probe according to claim 1, further comprising a second acoustic matching layer disposed between the acoustic matching layer and the plurality of piezoelectric elements and which is divided to be individually arranged correspondingly to the respective plurality of piezoelectric elements.
3. The ultrasonic probe according to claim 1, wherein the acoustic matching layer is mainly composed of synthetic rubber, silicon rubber, urethane rubber, or elastomer.
4. The ultrasonic probe according to claim 3, wherein the synthetic rubber is mainly composed of ethylene-propylene copolymer rubber, chloroprene rubber, butadiene rubber, isoprene rubber, styrene-butadiene copolymer rubber, or acrylonitrile-butadiene copolymer rubber.
5. The ultrasonic probe according to claim 1, wherein the acoustic matching layer is formed of a rubber elastic material which is continuous and undivided, spans the gap, and extends over the surface of each of the plurality of piezoelectric elements.

6. The ultrasonic probe according to claim 1, wherein the acoustic impedance of the acoustic matching layer is in a range of 1.8 to 2.2 MRayls.

7. The ultrasonic probe according to claim 1, wherein the acoustic matching layer is formed of a film which has a substantially uniform thickness.

8. The ultrasonic probe according to claim 1, further comprising:
an acoustic lens provided on a subject side of the plurality of piezoelectric elements,
wherein the acoustic matching layer is provided between the plurality of piezoelectric elements and the acoustic lens.

9. The ultrasonic probe according to claim 1, wherein the acoustic matching layer is formed of a rubber elastic material.

10. An ultrasonic probe, comprising:
a plurality of piezoelectric elements which are spaced apart from each other;
a third acoustic matching layer which extends as a continuous, undivided single layer over a surface of each of the plurality of piezoelectric elements and has an acoustic impedance in a range of 1.8 to 2.2 MRayls and an acoustic velocity of 1650 m/sec or less; and
first and second acoustic matching layers each of which is divided to be individually arranged correspondingly to the respective plurality of piezoelectric elements and which are provided between the third acoustic matching layer and the plurality of piezoelectric elements.

11. The ultrasonic probe according to claim 10, wherein the third acoustic matching layer is formed of a rubber elastic material.

12. The ultrasonic probe according to claim 11, wherein the rubber elastic material is mainly composed of synthetic rubber, silicon rubber, urethane rubber, or elastomer.

13. The ultrasonic probe according to claim 12, wherein the synthetic rubber is mainly composed of ethylene-propylene copolymer rubber, chloroprene rubber, butadiene rubber, isoprene rubber, styrene-butadiene copolymer rubber, or acrylonitrilebutadiene copolymer rubber.

14. The ultrasonic probe according to claim 10, wherein the third acoustic matching layer is formed of a film which has a substantially uniform thickness.

15. The ultrasonic probe according to claim 10, further comprising:
an acoustic lens provided on a subject side of the plurality of piezoelectric elements,
wherein the third acoustic matching layer is provided between the plurality of piezoelectric elements and the acoustic lens.

16. The ultrasonic probe according to claim 10, further comprising:
a first film which is provided on first surfaces of the plurality of piezoelectric elements, the first surfaces being opposite to the surfaces of the plurality of piezoelectric elements on which the first acoustic matching layer, the second acoustic matching layer, and the third acoustic matching layer are formed, and which comprises a plurality of electric terminals provided to correspond to the respective plurality of piezoelectric elements.

17. The ultrasonic probe according to claim 10, further comprising:
a first film which is provided between the first acoustic matching layer and the second acoustic matching layer, and which comprises a plurality of electric terminals which correspond to the respective plurality of piezoelectric elements.

18. An ultrasonic probe, comprising:
a plurality of piezoelectric elements which are spaced apart from each other;
second and third acoustic matching layers, each of which extends as a continuous, undivided single layer over a surface of all of the plurality of piezoelectric elements and has an acoustic velocity of 1650 m/sec or less; and
a first acoustic matching layer provided between Ill the second and third acoustic matching layers and al the plurality of piezoelectric elements.

19. The ultrasonic probe according to claim 18, wherein the first acoustic matching layer is divided to be individually arranged correspondingly to the respective plurality of piezoelectric elements.

20. The ultrasonic probe according to claim 18, wherein the second and third acoustic matching layers are formed of a rubber elastic material.

21. The ultrasonic probe according to claim 20, wherein the rubber elastic material is mainly composed of synthetic rubber, silicon rubber, urethane rubber, or elastomer.

22. The ultrasonic probe according to claim 21, wherein the synthetic rubber is mainly composed of ethylene-propylene copolymer rubber, chloroprene rubber, butadiene rubber, isoprene rubber, styrene-butadiene copolymer rubber, or acrylonitrilebutadiene copolymer rubber.

23. An ultrasonic probe, comprising:
a plurality of piezoelectric elements which are spaced apart from each other;
a fourth acoustic matching layer which extends as a continuous, undivided single layer across a surface of each of the plurality of piezoelectric elements and has an acoustic velocity of 1650 m/sec or less; and
first, second and third acoustic matching layers provided between the fourth acoustic matching layer and the plurality of piezoelectric elements.

24. The ultrasonic probe according to claim 23,
wherein the fourth acoustic matching layer is provided on the surface of the plurality of piezoelectric elements, and
wherein the first, second and third acoustic matching layers are divided to be individually arranged correspondingly to the respective plurality of piezoelectric elements.

25. The ultrasonic probe according to claim 23,
wherein the third acoustic matching layer and the fourth acoustic matching layer are provided on the surface of the plurality of piezoelectric elements, each extending as a continuous, undivided single layer across the surface of each of the plurality of piezoelectric elements, and
wherein each of the first acoustic matching layer and the second acoustic matching layer is divided to be individually arranged correspondingly to the respective plurality of piezoelectric elements.

26. The ultrasonic probe according to claim 25, wherein each of the third and fourth acoustic matching layers is formed of a rubber elastic material and has an acoustic velocity of 1650 m/sec or less.

27. The ultrasonic probe according to claim 23, wherein the fourth acoustic matching layer is formed of a rubber elastic material.

28. The ultrasonic probe according to claim 27, wherein the rubber elastic material is mainly composed of synthetic rubber, silicon rubber, urethane rubber, or elastomer.

29. The ultrasonic probe according to claim 28, wherein the synthetic rubber is mainly composed of ethylene-propylene copolymer rubber, chloroprene rubber, butadiene rubber, isoprene rubber, styrene-butadiene copolymer rubber, or acrylonitrilebutadiene copolymer rubber.

30. An ultrasonic probe, comprising:
- a plurality of piezoelectric elements which are separated from each other by a gap;
- a first acoustic matching layer which extends as a continuous, undivided single layer over a surface of the plurality of piezoelectric elements;
- a second acoustic matching layer provided between the first acoustic matching layer and the plurality of piezoelectric elements and which is divided to be individually arranged correspondingly to the respective plurality of piezoelectric elements; and
- a film having an electric terminal provided between the first acoustic matching layer and the second acoustic matching layer and which is divided to be individually arranged correspondingly to the respective plurality of piezoelectric elements.

31. The ultrasonic probe according to claim 30, wherein the first acoustic matching layer is formed of a material that has an acoustic velocity of 1650 m/sec or less.

32. The ultrasonic probe according to claim 30, wherein the first acoustic matching layer is formed of a rubber elastic material.

33. The ultrasonic probe according to claim 30, further comprising a third acoustic matching layer disposed between the film and the first acoustic matching layer.

* * * * *